US007317014B2

(12) United States Patent
Agarwal et al.

(10) Patent No.: US 7,317,014 B2

(45) Date of Patent: Jan. 8, 2008

(54) BIO-ACTIVE PYRIMIDINE MOLECULES

(75) Inventors: Shiv Kumar Agarwal, Chennai (IN); Ravikumar Tadiparthi, Chennai (IN); Pawan Aggarwal, Chennai (IN); Savithiri Shivakumar, Chennai (IN)

(73) Assignees: Orchid Research Laboratories, Ltd., Nangambakkam (IN); Bexel Pharmaceuticals Inc., Union City ( * ) Notice: Subject to any disclaimer, the term of this patent is extended or adjusted under 35 U.S.C. 154(b) by 429 days.

(21) Appl. No.: 10/469,647

(22) PCT Filed: Jul. 21, 2003

(86) PCT No.: PCT/IB03/02879

§ 371 (c)(1), (2), (4) Date: Sep. 3, 2003

(87) PCT Pub. No.: WO2004/009560

PCT Pub. Date: Jan. 29, 2004

(65) Prior Publication Data

US 2005/0107413 A1 May 19, 2005

(30) Foreign Application Priority Data

Jul. 22, 2002 (IN) ......................... 548/MAS/2002

(51) Int. Cl.

*C07D 239/30* (2006.01)
*C07D 239/48* (2006.01)
*A61K 31/505* (2006.01)

(52) U.S. Cl. ...................... 514/256; 514/269; 514/274; 544/315; 544/319; 544/334; 544/335

(58) Field of Classification Search ................ 544/315, 544/319, 334, 335; 514/256, 269, 274
See application file for complete search history.

(56) References Cited

U.S. PATENT DOCUMENTS

| | | | | | |
|---|---|---|---|---|---|
| 2,602,794 | A | * | 7/1952 | Hitchings et al. | 544/325 |
| 3,772,288 | A | * | 11/1973 | Hardtmann et al. | 544/315 |
| 4,438,117 | A | * | 3/1984 | Cherkofsky | 514/274 |
| 4,771,040 | A | | 9/1988 | Maurer et al. | |
| 5,118,686 | A | * | 6/1992 | Coates et al. | 514/269 |
| 5,580,985 | A | * | 12/1996 | Lee et al. | 548/364.1 |
| 6,410,729 | B1 | | 6/2002 | Spohr et al. | |
| 6,420,385 | B1 | | 7/2002 | Spohr et al. | |
| 6,867,205 | B2 | * | 3/2005 | Boehringer et al. | 514/217.06 |
| 2003/0225075 | A1 | * | 12/2003 | Agarwal et al. | 514/227.8 |

FOREIGN PATENT DOCUMENTS

| | | | |
|---|---|---|---|
| DE | 2142317 | | 3/1973 |
| EP | 130046 | * | 1/1985 |
| WO | WO 92/02513 | * | 2/1992 |

OTHER PUBLICATIONS

Douglas, Jr. Introduction to viral diseases, Cecil Textbook of Medicine, 20th Edition, vol. 2, pp. 1739-1747, 1996.*
Simone, Oncology: Introduction, Cecil Textbook of Medicine, 20th Edition, vol. 1, pp. 1004-1010, 1996.*
Casanova et al., PubMed Abstract (Rev Neurol. 28(9):909-15) May 1999.*
Freston, PubMed Abstract (Am J Med 107(6A):78S-88S; discussions) Dec. 1999.*
Naesdal et al., PubMed Abstract (Eur J Gastroenterol Hepatol. 13(12):1401-6) Dec. 2001.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, Aug. 2002.*
Hannah et al., CAPLUS Abstract 133:105004, 2000.*
Koyama et al., CAPLUS Abstract 78:4210, 1973.*
Koyama et al., CAPLUS Abstract 72:90403, 1970.*
Chase et al., CAPLUS Abstract 49:36033, 1955.*
Tagawa, PubMed Abstract (Curr Pharm Des. 6(6):681-99), Apr. 2000.*
*Cutting Edge Reports* available at http://www.rheuma21st.com/archives/winter_symposium.html, Feb. 23, 2000.
Garderova, et al., "The Use of TNF Family Ligands and Receptors and Agents which Modify their Interaction as Therapeutic Agents," *Current Drug Targets*, vol. 1, pp. 327-364, 2000.
Israel, A., "The IKK Complex: an integrator of all signals that activate NF-κB," Trends Cell Biol., vol. 10, pp. 129-133 (2000).
Liou, et al., "Regulation of the NF-κB/rel transcription factor and IκB inhibitor system," Current Opinion in Cell Biology, vol. 5, pp. 477-487, 1993.
Israel, A., "A role for phosphorylation and degradation in the control of NF-κB," Trends Cell Biol., vol. 11, No. 6, pp. 203-205, 1995.
Gilmore, et al., "The I κB proteins:members of a multifunctional family," Trends Genet., vol. 9, No. 12, pp. 427-433, 1993.
Anderson, "Toll signaling pathways in the innate immune response," Curr. Opin. Immunol. vol. 12, pp. 13-19, 2000.

(Continued)

*Primary Examiner*—Deepak Rao
(74) *Attorney, Agent, or Firm*—Oliff & Berridge, PLC.

(57) ABSTRACT

The present invention relates to novel derivatives of the general formula (I), their derivatives, their analogs, their tautomeric forms, their stereoisomers, their polymorphs, their hydrates, their solvates, their pharmaceutically acceptable salts and pharmaceutically acceptable compositions containing them. The present invention more particularly provides novel pyrimidine derivatives of the general formula (I)

(I)

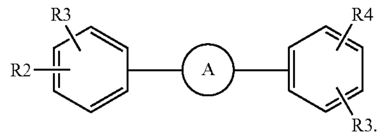

20 Claims, No Drawings

OTHER PUBLICATIONS

Sen, et al., "Multiple Nuclear Factors Interact with the Immunoglobulin Enhancer Sequences," Cell, vol. 46, pp. 705-716, 1986.
Zhang, et al., "Toll-like receptor-mediated NF-B activation: a phylogenetically conserved paradigm in innate immunity," Clin. Invest., vol. 107, pp. 13-19, 2001.
Scheinmann, et al., "Role of Transcriptional Activation of IκBα in Mediation of Immunosuppression by Glucocorticoids," Science, vol. 270, pp. 28386, 1995.
Davis, et al., "Rel-Associated pp. 40: An Inhibitor of the Rel Family of Transcription Factors," Science, vol. 253, pp. 1268-1271, 1991.
Demarachi, et al., "Activation of Transcription Factor NF-κB by the Tat Protein of Human Immunodeficiency Virus Type 1," J. Virol., vol. 7, pp. 4427-4437, 1996.
Sha, et al., "Targeted Disruption of the p50 Subunit of NF-κB Leads to Multifocal Defects in Immune Responses," Cell, vol. 80, pp. 321-330, 1995.
Beg, et al, "Embryonic lethality and liver degeneration in mice lacking the RelA components of NF-κB," Nature, vol. 376, pp. 167-170, 1995.
Weih, et al., "Multiorgan Inflammation and Hematopoietic Abnormalities in Mice with a Targeted Disruption of RelB, a Member of the NF-κB/Rel Family," Cell, vol. 80, pp. 331-340, 1995.
Burkly, et al., "Expression of relB is required for the development of thymic medulla and dendritic cells," Nature, vol. 373, pp. 531-536, 1995.
Tak, et al., "NF-κB: a key role in inflammatory diseases," J. Clin. Invest., vol. 107, pp. 7-11, 2001.
Yamamoto, et al., "Therapeutic potential of inhibition of the NF-κB pathway in the treatment of inflammation and cancer," J. Clin. Invest. , vol. 107, pp. 135-142, 2001.
Pahl, "Activators and target genes of Rel/NF-κB transcription factors," Oncogene, vol. 18, pp. 6853-6866, 1999.
Nguyen, et al, "Chemogenomic identification of Ref-1/Ap-1 as a therapeutic target for asthma," PNAS, vol. 100, No. 3, pp. 1169-1173, 2003.
Grootendorst, et al., "Efficacy of the novel phosphodiesterase-4 inhibitor BAY 19-8004 on lung function and airway inflammation in asthma and chronic obstructive pulmonary disease (COPD)," Pulmonary Pharmacology and Therapeutics, vol. 16, pp. 341-347, 2003.
Rabinowitz, et al., "Design of Selective and Soluble Inhibitors of Tumor Necrosis Factor-α Converting Enzyme (TACE)," J.Med. Chem, vol. 44, pp. 4252-4267, 2001.
van den Brink, et al., "Expression and Activation of NF-κB in the Antrum of the Human Stomach," J.Immunol., vol. 164. pp. 3353-3359, 2000.
Schreiber, et al., "Activation of nuclear factor κB in inflammatory bowel disease," Gut, vol. 42, pp. 477-484, 1998.
Jobin, et al., "The IκB/NF-κB system: a key determinant of mucosal inflammation and protection," Am.J. Physiol.Cell Phsiol., vol. 278, C451-C462, 2000 (review).
Tak, et al., "NF-κB: a key role in inflammatory disease," The Journal of Clinical. Investigation, vol. 107, No. 1, pp. 7-11 2001.
van Heel, et al., "Inflammatory bowel disease is associated with a TNF polymorphism that affects an interaction between the OCT1 and NF-κB transcription factors," Human Molecular Genetics, vol. 11, No. 11, pp. 1281-1289, 2002.
Farrel, et al., "Mechanisms of Steroid Action and Resistance in Inflammation," Journal of Endocrinology, Vo. 178, pp. 339-346, 2003.
Brand, et al., "Activated Transcription Factor Nuclear Factor-Kappa B is Present in the Aterosclerotic Lesion," J. Clin. Invest., vol. 97, pp. 1715-1722, 1996.
Wilson, et al., "Activated nuclear factor-κB is present in the coronary vasculature in experimental hypercholesterolemia," Atherosclerosis, vol. 148, pp. 23-30, 2000.
Cheng, et al., "NF-κB Subunit-specific Regulation of the IκBα Promoter," J. Biol. Chem., vol. 296, pp. 13351-13557, 1994.
Bowie, et al., "Lipid Peroxidation Is Involved in the Activation of NF-κB by Tumor Necrosis Factor by Not Interleukin-1 in the Human Endothelial Cell Lin ACV304," J. Biol. Chem., vol. 272, pp. 25941-25950, 1997.
Ozaki, et al., "Overexpression of redox factor-1 protects against postischemic liver injury by reducing oxidative stress and NF-κB," Transplant, vol. 34, No. 7, pp. 2640-2642, 2002 (Abstract only).
Meister, "Glutathione-Ascorbic Acid Antioxidant System in Animals," J. Biol. Chem., vol. 269, pp. 9397-9400, 1994.
Hagen, et al., "Bioavailability of dietary glutatione: effect on plasma concentration," Am. J. Physiol., vol. 259, pp. 524-529, 1990.
Cho, et al., "Glutatione Downregulates the Phosphorylation of IκB: Autoloop Regulation of the NF-κB-Mediated Expression of NF-κB Subunits by TNF-α in Mouse Vascular Endothelial Cells," Biochem. Biophys. Res. Commun., vol. 253, pp. 104-108, 1998.
Simon, et al., "Effects of glutathione precursors on human immunodeficiency virus replication," Chem. Biol. Interact., vol. 91, pp. 217-224, 1994.
Sen, et al., "A Positively Charged α-Lipoic Acid Analogue with Increased Cellular Uptake and More Potent Immunomodulatory Activity," Biochem. Biophys.Res. Commun., vol. 247, pp. 223-228, 1998.
De Vries, N.; De Flora, S. *J. Cell.Biochem.* 1993, 17F, 3270.
Ferran, et al., "Inhibition of NF-κB by Pyrrolidine Dithiocarbamate Blocks Endothelial Cell Activation," Biochem. Biophys. Res. Commun., vol. 214, pp. 212-223, 1995.
Schreck, et al., "Dithiocarbamates as Potent Inhibitors of Nuclear Factor κB Activation in Intact Cells," J. Exp. Med., vol. 175, pp. 1181-1194, 1992.
Yan, et al., "Aminosalycylic Acid Inhibits IκB Kinase α Phosphorylation of IκBα in Mouse Intestincal Epithelial Cells," J. Biol. Chem., vol. 274, pp. 36631-36636, 1999.
Yamamoto, et al., "Sulindac Inhibits Activation of the NFκB Pathway," J. Biol Chem., vol. 274, pp. 27307-27314, 1999.
Chu, et al., "The Tax Oncoprotein of Human T-cell Leukemia Virus Type 1 Associates with and Persistently Activates IκB Kinases Containing IKKα and IKKβ," J. Biol. Chem., vol. 273, pp. 15891-15894, 1998.
Baldwin, "Control of oncogenesis and cancer therapy resistance by the transcription factor NF-κB," J. Clin. Invest., vol. 107, pp. 241-246, 2001.
Mosialos, "The role of Rel/NF-κB proteins in viral oncogenesis and the regulation of viral transcription," Seminars in Cancer Biololigy, vol. 8, pp. 121-129, 1997.
Libby, "Molecular Bases of the Acute Coronary Syndromes," Circulation, vol. 91, pp. 2844-2850, 1995.
Falk, et al., "Coronary Plaque Disruption," Circulation, vol. 92, pp. 657-671, 1995.
Dannhardt, et al., "Cylcooxygense inhibitors-current status and future prospects," Eur.J.Med.Chem. vol. 36, pp. 109-126, 2001.
Hu, et al., "Chemoprevention of Gastric Cancer by Celecoxib in Rats," *Gut*, vol. 53, pp. 195-200, 2004.

* cited by examiner

BIO-ACTIVE PYRIMIDINE MOLECULES

This application is a 371 of PCT/IB03/02879 filed Jul. 21, 2003.

FIELD OF THE INVENTION

The present invention relates to novel compounds of the general formula (I), their derivatives, their analogs, their tautomeric forms, their stereoisomers, their polymorphs, their hydrates, their solvates, their pharmaceutically acceptable salts and pharmaceutically acceptable compositions containing them. The present invention more particularly provides novel pyrimidine derivatives of the general formula (I).

(I)

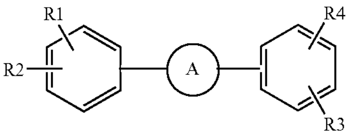

The present invention also provides a process for the preparation of the above said novel compounds of the formula (I) pharmaceutically acceptable salts, their derivatives, their analogs, their tautomeric forms, their stereoisomers, their polymorphs, their hydrates, their solvates, their pharmaceutically acceptable salts, and pharmaceutical compositions containing them.

The novel compounds of the present invention are useful for the treatment of inflammation and immunological diseases. Particularly the compounds of the present invention are useful for the treatment of inflammation and immunological diseases those mediated by cytokines such as TNF-α, IL-1, IL-6, IL-1β, IL-8 and cyclooxygenase such as COX-1, COX-2 and COX-3. The compounds of the present invention are also useful for the treatment of rheumatoid arthritis; osteoporosis; multiple myeloma; uveititis; acute and chronic myelogenous leukemia; ischemic heart disease, atherosclerosis, cancer, ischemic-induced cell damage, pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever and myalgias due to infection; and diseases mediated by HIV-1; HIV-2; HIV-3; cytomegalovirus (CMV); influenza; adenovirus; the herpes viruses (including HSV-1, HSV-2) and herpes zoster viruses.

BACKGROUND OF INVENTION

It has been reported that Cyclooxygenase enzyme exists in three isoforms, namely, COX-1, COX-2 and COX-3. COX-1 enzyme is essential and primarily responsible for the regulation of gastric fluids whereas COX-2 enzyme is present at the basal levels and is reported to have a major role in the prostaglandin synthesis for inflammatory response. These prostaglandins are known to cause inflammation in the body. Hence, if the synthesis of these prostaglandins is stopped by way of inhibiting COX-2 enzyme, inflammation and its related disorders can be treated. COX-3 possesses glycosylation-dependent cyclooxygenase activity. Comparison of canine COX-3 activity with murine COX-1 and COX-2 demonstrated that this enzyme is selectively inhibited by analgesic/antipyretic drugs such as acetaminophen, phenacetin, antipyrine, and dipyrone, and is potently inhibited by some nonsteroidal antiinflammatory drugs. Thus, inhibition of COX-3 could represent a primary central mechanism by which these drugs decrease pain and possibly fever. Recent reports show that inhibitors of COX-1 enzyme causes gastric ulcers, where as selective COX-2 and COX-3 enzyme inhibitors are devoid of this function and hence are found to be safe.

The present invention is concerned with treatment of immunological diseases or inflammation, notably such diseases are mediated by cytokines or cyclooxygenase. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL-1, IL-12 and TNF-α all of which are potent pro-inflammatory molecules and also provide help for T cells. In addition, activation of macrophages results in the induction of enzymes, such as cyclooxygenase-2 (COX-2) and cyclooxygenase-3 (COX-3), inducible nitric oxide synthase (iNOS) and production of free radicals capable of damaging normal cells. Many factors activate macrophages, including bacterial products, superantigens and interferon gamma (IFN γ). It is believed that phosphotyrosine kinases (PTKs) and other undefined cellular kinases are involved in the activation process.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-α) plays a central role in the inflammatory response and has been targeted as a point of intervention in inflammatory disease. TNF-α is a polypeptide hormone released by activated macrophages and other cells. At low concentrations, TNF-α participates in the protective inflammatory response by activating leukocytes and promoting their migration to extravascular sites of inflammation (Moser et al., J. Clin. Invest., 83, 444-55,1989). At higher concentrations, TNF-α can act as a potent pyrogen and induce the production of other pro-inflammatory cytokines (Haworth et al., Eur. J. Immunol., 21, 2575-79, 1991; Brennan et al., Lancet, 2, 244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum., 38, 151-60, 1995). Inhibitors of TNF-α, including soluble TNF receptors (etanercept) (Goldenberg, Clin Ther., 21, 75-87, 1999) and anti-TNF-α antibody (infliximab) (Luong et al., Ann Pharmacother., 34, 743-60, 2000), have recently been approved by the U.S. Food and Drug Administration (FDA) as agents for the treatment of rheumatoid arthritis.

Elevated levels of TNF-α have also been implicated in many other disorders and disease conditions, including cachexia, septic shock syndrome, osteoarthritis, inflammatory bowel disease such as Crohn's disease and ulcerative colitis etc.

Elevated levels of TNF-α and/or IL-1 over basal levels have been implicated in mediating or exacerbating a number of disease states including rheumatoid arthritis; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It can be seen that inhibitors of TNF-α are potentially useful in the treatment of a wide variety of diseases. Compounds that inhibit TNF-α have been described in several patents.

Excessive production of IL-6 is implicated in several disease states, it is highly desirable to develop compounds that inhibit IL-6 secretion. Compounds that inhibit IL-6 have been described in U.S. Pat. Nos. 6,004,813; 5,527,546 and 5,166,137.

The cytokine IL-1β also participates in the inflammatory response. It stimulates thymocyte proliferation, fibroblast growth factor activity, and the release of prostaglandin from synovial cells. Elevated or unregulated levels of the cytokine IL-1β have been associated with a number of inflammatory diseases and other disease states, including but not limited to adult respiratory distress syndrome, allergy, Alzheimer's disease etc. Since overproduction of IL-1β is associated with numerous disease conditions, it is desirable to develop compounds that inhibit the production or activity of IL-1β.

In rheumatoid arthritis models in animals, multiple intra-articular injections of IL-1 have led to an acute and destructive form of arthritis (Chandrasekhar et al., Clinical Immunol Immunopathol., 55, 382, 1990). In studies using cultured rheumatoid synovial cells, IL-1 is a more potent inducer of stromelysin than TNF-α. (Firestein, Am. J. Pathol., 140, 1309, 1992). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokine Net., 5, 517-531, 1994).

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice) intra-articular administration of TNF-α either prior to or after the induction of CIA led to an accelerated onset of arthritis and a more severe course of the disease (Brahn et al., Lymphokine Cytokine Res., 11, 253, 1992; and Cooper, Clin. Exp. Immunol., 898, 244, 1992).

IL-8 has been implicated in exacerbating and/or causing many disease states in which massive neutrophil in filtration into sites of inlammation or injury (e.g., ischemia) is mediated chemotactic nature of IL-8, including, but not limited to, the following: asthma, inflammatory bowl disease, psoriasis, adult respiratory distress syndrome, cardiac and renal reperfusion injury, thrombosis and glomerulonephritis. In addition to the chemotaxis effect on neutrophils, IL-8 has also has ability to activate neutrophils. Thus, reduction in IL-8 levels may lead to diminished neutrophil infiltration.

Few prior art reference which disclose the closest pyrimidine compounds are given here:

i) U.S. Pat. No. 6,420,385 discloses novel compounds of formula (IIa)

(IIa)

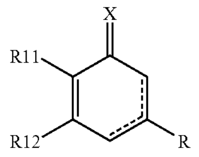

wherein

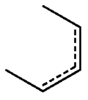

represents

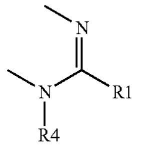

or

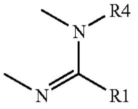

X is O, S or $NR_5$; $R_1$ and $R_2$ each independently represent —Y or —Z—Y, and $R_3$ and $R_4$ each independently —Z—Y or $R_3$ is a hydrogen radical; provided that $R_4$ is other than a substituted-aryl, (substituted-aryl)methyl or (substituted-aryl)ethyl radical; wherein each Z is independently optionally substituted alkyl, alkenyl, alkynyl, heterocyclyl, aryl or heteroaryl; Y is independently a hydrogen; halo, cyano, nitro, etc., $R_5$ is independently a hydrogen, optionally substituted alkyl, alkenyl, alkynyl etc., $R_{11}$ and $R_{12}$ are each independently represent optionally substituted aryl or heteroaryl.

An example of these compounds is shown in formula (IIb)

(IIb)

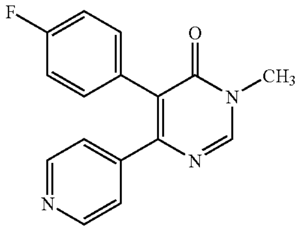

ii) DE 2142317 discloses hypnotic uracil derivatives of formula (IIc)

(IIc)

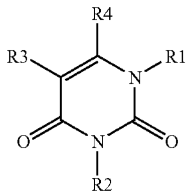

wherein $R_1$ is H, alkyl, alkenyl, dialkylaminoalkyl, or aralkyl; $R_2$ is H, alkyl, aryl, or halogen; $R_3$ is alkyl, alkenyl, cycloalkyl, aralkyl, aralkenyl, or aryl, $R_4$ is alkyl, alkenyl, cycloalkyl, aralkyl, aryl, etc.

An example of these compounds is shown in formula (IId)

(IId)

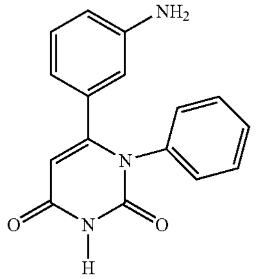

iii) U.S. Pat. Nos. 6,420,385 and 6,410,729 discloses novel compounds of formula (IIe)

(IIe)

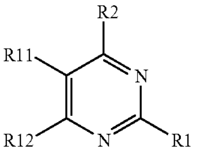

wherein $R_1$ and $R_2$ are each independently —Z—Y, preferably, $R_2$ is a radical of hydrogen, $C_1$-$C_4$ alkyl, halo, hydroxy, amino, etc., Z is independently a bond, alkyl, alkenyl etc., Y is independently a hydrogen radical, halo, nitro radical; $R_{20}$ is independently (1) alkyl, alkenyl, heterocyclyl radical, aryl, heteroaryl; $R_{21}$ is independently hydrogen radical, $R_{20}$; $R_{22}$ is independently hydrogen, heterocyclyl, aryl or heteroaryl

OBJECTIVE OF THE INVENTION

We have focused our research to identify selective COX-1, COX-2 and COX-3 inhibitors, which are devoid of any side effects normally associated with anti-inflammatory agents. Our sustained efforts have resulted in novel compounds of the formula (I). The derivatives may be useful in the treatment of inflammation and immunological diseases. Particularly the compound of the present invention are useful for the treatment of inflammation and immunological diseases those mediated by cytokines such as TNF-α, IL-1, IL-6, IL-1β, IL-8 and cyclooxygenase such as COX-1, COX-2 and COX-3. The compound of the present invention are also useful for the treatment of rheumatoid arthritis; osteoporosis; multiple myeloma; uveititis; acute and chronic myelogenous leukemia; ischemic heart disease; atherosclerosis; cancer; ischemic-induced cell damage; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection; and diseases mediated by HIV-1; HIV-2; HIV-3; cytomegalovirus (CMV); influenza; adenovirus; the herpes viruses (including HSV-1, HSV-2) and herpes zoster viruses.

SUMMARY OF THE INVENTION

The present invention relates to novel pyrimidine derivatives of the formula (I)

(I)

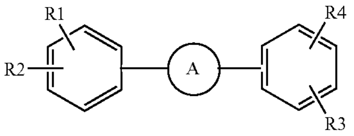

their derivatives, their analogs, their tautomeric forms, their stereoisomers, their polymorphs, their solvates, their pharmaceutically acceptable salts and their pharmaceutically acceptable compositions, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid or its derivatives; A represents pyrimidine derivative of the formula

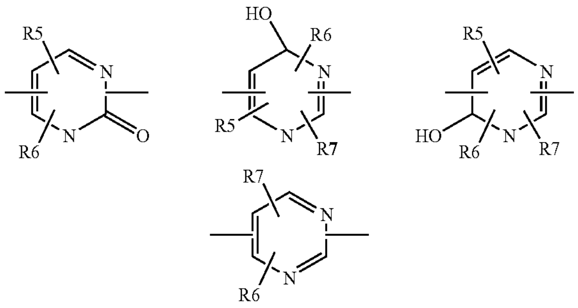

wherein $R_5$, $R_6$, $R_7$, may be same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid or its derivatives; the pyrimidine group may be attached to the phenyl through carbon or nitrogen atom.

DETAILED DESCRIPTION OF THE INVENTION

Suitable groups represented by $R_1$, $R_2$, $R_3$, $R_4$, are selected from hydrogen, hydroxy, nitro, nitroso, formyl, azido, halogen atom such as fluorine, chlorine, bromine or iodine; or substituted or unsubstituted linear or branched ($C_1$-$C_6$) alkyl group, such as methyl, ethyl, n-propyl, isopropyl, n-butyl, isobutyl, t-butyl, n-pentyl, isopentyl, hexyl and the like; haloalkyl such as chloromethyl, chloroethyl, trifluoromethyl, trifluoroethyl, dichloromethyl, dichloroethyl and the like, which may be substituted; aryl group such as phenyl or naphthyl, the aryl group may be substituted; cyclo ($C_3$-$C_6$) alkyl group such as cyclopropyl, cyclobutyl, cyclopentyl, cyclohexyl and the like, the cycloalkyl group may be substituted; acyl group such as —C(=O)$CH_3$, —C(=O)$C_2H_5$, —C(=O)$C_3H_7$, —C(=O)$C_6H_{13}$, —C(=S)$CH_3$, —C(=S)$C_2H_5$, —C(=S)$C_3H_7$, —C(=S)$C_6H_{13}$, benzoyl and the like, which may be substituted; linear or branched ($C_1$-$C_6$) alkoxy group, such as methoxy, ethoxy, n-propoxy, isopropoxy and the like; aryloxy group such as phenoxy, napthoxy, the aryloxy group may be substituted; aralkoxy group such as benzyloxy, phenethyloxy and the like, which may be substituted; acyloxy group such as MeCOO—, EtCOO—, PhCOO— and the like, which may be substituted; heterocyclyl groups such as pyrrolidinyl, morpholinyl, thiomorpholinyl, piperidinyl, piperazinyl, and the like, the heterocyclyl group may be substituted; heteroaryl group may be mono or fused system such as pyridyl, thienyl, furyl, pyrrolyl, oxazolyl, thiazolyl, imidazolyl, oxadiazolyl, thiadiazolyl, tetrazolyl, pyrimidinyl, pyrazine, piperazine, benzopyranyl, benzofuranyl, benzimidazolyl, benzoxazolyl, benzothiazolyl, benzopyrrolyl, benzoxadiazolyl, benzothiadiazolyl and the like, the heteroaryl group may be substituted; aralkyl group such as benzyl, phenylethyl, phenyl propyl and the like, which may be substituted; amino, which may be substituted; hydrazine, which may be substituted; monoalkylamino group such as —$NHCH_3$, —$NHC_2H_5$, —$NHC_3H_7$, —$NHC_6H_{13}$, and the like, which may be substituted; dialkylamino group such as —$N(CH_3)_2$, —$NCH_3(C_2H_5)$, —$N(C_2H_5)_2$ and the like, which may be substituted; acylamino group such as —NHC(=O)$CH_3$, —NHC(=O)$C_2H_5$, —NHC(=O)$C_3H_7$, —NHC(=O)$C_6H_{13}$, and the like, which may be substituted; alkoxycarbonyl group such as methoxycarbonyl, ethoxycarbonyl, n-propoxycarbonyl, isopropoxycarbonyl and the like, the alkoxycarbonyl group may be substituted; aryloxycarbonyl group such as phenoxycarbonyl, napthoxycarbonyl, the aryloxycarbonyl group may be substituted; alkylsulfonyl group such as methylsulfonyl, ethylsulfonyl, n-propylsulfonyl, isopropylsulfonyl and the like, the alkylsulfonyl group may be substituted; arylsulfonyl group such as phenylsulfonyl or naphthylsulfonyl, the arylsulfonyl group may be substituted; alkylsulfinyl group such as methylsulfmyl, ethylsulfmyl, n-propylsulfinyl, iso-propylsulfinyl and the like, the alkylsulfmyl group may be substituted; arylsulfmyl group such as phenylsulfmyl or naphthylsulfmyl, the arylsulfmyl group may be substituted; alkylthio group such as methylthio, ethylthio, n-propylthio, iso-propylthio and the like, the alkylthio group may be substituted; arylthio group such as phenylthio, or naphthylthio, the arylthio group may be substituted; alkoxyalkyl group such as methoxymethyl, ethoxymethyl, methoxyethyl, ethoxyethyl and the like, which may be substituted; sulfamoyl; carboxylic acid or its derivatives. Examples of derivatives of the carboxylic acid may be esters, amides, and acid halides.

Suitable groups represented by $R_5$, $R_6$ and $R_7$ are selected from hydrogen, nitro, nitroso, formyl, azido, halo; substituted or unsubstituted linear or branched ($C_1$-$C_6$) alkyl group, such as methyl, ethyl, n-propyl, isopropyl, n-butyl, isobutyl, t-butyl, n-pentyl, isopentyl, hexyl and the like; linear or branched ($C_1$-$C_6$) alkoxy group, such as methoxy, ethoxy, n-propoxy, isopropoxy and the like; acyl group such as —C(=O)$CH_3$, —C(=O)$C_2H_5$, —C(=O)$C_3H_7$, —C(=O)$C_6H_{13}$, —C(=S)$CH_3$, —C(=S)$C_2H_5$, —C(=S)$C_3H_7$, —C(=S)$C_6H_{13}$, benzoyl and the like, which may be substituted; cyclo ($C_3$-$C_6$) alkyl group such as cyclopropyl, cyclobutyl, cyclopentyl, cyclohexyl and the like, the cycloalkyl group may be substituted; haloalkyl such as chloromethyl, chloroethyl, trifluoromethyl, trifluoroethyl, dichloromethyl, dichloroethyl and the like, which may be substituted; amino, which may be substituted; hydrazine, which may be substituted; alkoxyalkyl group such as methoxymethyl, ethoxymethyl, methoxyethyl, ethoxyethyl and the like, which may be substituted; monoalkylamino group such as —$NHCH_3$, —$NHC_2H_5$, —$NHC_3H_7$, —$NHC_6H_{13}$, and the like, which may be substituted; dialkylamino group such as —$N(CH_3)_2$, —$NCH_3(C_2H_5)$, —$N(C_2H_5)_2$ and the like, which may be substituted; acylamino group such as —NHC(=O)$CH_3$, —NHC(=O)$C_2H_5$, —NHC(=O)$C_3H_7$, —NHC(=O)$C_6H_{13}$, and the like, which may be substituted; alkylsulfonyl group such as methylsulfonyl, ethylsulfonyl, n-propylsulfonyl, iso-propylsulfonyl and the like, the alkylsulfonyl group may be substituted; arylsulfonyl group such as phenylsulfonyl or naphthylsulfonyl, the arylsulfonyl group may be substituted; alkylsulfinyl group such as methylsulfinyl, ethylsulfinyl, n-propylsulfmyl, iso-propylsulfinyl and the like, the alkylsulfinyl group may be substituted; arylsulfinyl group such as phenylsulfmyl or naphthylsulfinyl, the arylsulfmyl group may be substituted; alkylthio group such as methylthio, ethylthio, n-propylthio, iso-propylthio and the like, the alkylthio group may be substituted; arylthio group such as phenylthio, or naphthylthio, the arylthio group may be substituted; aryloxycarbonyl group such as phenoxycarbonyl, napthoxycarbonyl, the aryloxycarbonyl group may be substituted; alkoxycarbonyl group such as methoxycarbonyl, ethoxycarbonyl, n-propoxycarbonyl, isopropoxycarbonyl and the like, the alkoxycarbonyl group may be substituted; sulfamoyl; carboxylic acid or its derivatives such as esters, amides and acid halides.

When the groups $R_1$, $R_2$, $R_3$, $R_4$, $R_5$, $R_6$ and $R_7$ are substituted, the substituents may be selected from halogen, hydroxy, nitro, cyano, azido, nitroso, amino, hydrazine, formyl, alkyl, aryl, cycloalkyl, alkoxy, aryloxy, acyl, acyloxyacyl, heterocyclyl, heteroaryl, monoalkylamino, dialkylamino, acylamino, alkoxycarbonyl, aryloxycarbonyl, alkylsulfonyl, arylsulfonyl, alkylsulfmyl, arylsulfmyl, alkylthio, arylthio, sulfamoyl, alkoxyalkyl groups or carboxylic acids or its derivatives and these substituents are as defined above.

Pharmaceutically acceptable salts of the present invention include alkali metal like Li, Na, and K, alkaline earth metal like Ca and Mg, salts of organic bases such as diethanolamine, 60-phenylethylamine, benzylamine, piperidine, morpholine, pyridine, hydroxyethylpyrrolidine, hydroxyethylpiperidine, choline and the like, ammonium or substituted ammonium salts, aluminum salts. Salts also include amino acid salts such as glycine, alanine, cystine, cysteine, lysine, arginine, phenylalanine, guanidine etc. Salts may include acid addition salts where appropriate which are, sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Representative compounds according to the present invention include:

4-Chloro-5,6-diphenyl-2-(trifluoromethyl)pyrimidine;

4-Chloro-6-(4-methylphenyl)-5-phenyl-2-(trifluoromethyl) pyrimidine;

4-Chloro-6-(4-fluorophenyl)-5-phenyl-2-(trifluoromethyl) pyrimidine;

4-Chloro-6-[4-(methylsulfonyl)phenyl]-5-phenyl-2-(trifluoromethyl)pyrimidine;

4-Chloro-5-(4-chlorophenyl)-6-[4-(methylsulfonyl)phenyl]-2-(trifluoromethyl)pyrimidine;

4-Chloro-5-(4-fluorophenyl)-6-[4-(methylsulfonyl)phenyl]-2-(trifluoromethyl)pyrimidine;
2,4-Dichloro-5,6-diphenylpyrimidine;
2,4-Dichloro-6-(4-methylphenyl)-5-phenylpyrimidine;
6-(4-Chlorophenyl)-2,4-dichloro-5-phenylpyrimidine;
5-(4-Chlorophenyl)-2,4-dichloro-6-phenylpyrimidine;
2,4-Dichloro-5-(4-methoxyphenyl)-6-phenylpyrimidine;
2,4-Dichloro-5-[4-(methylthio)phenyl]-6-phenylpyrimidine;
2,4-Dichloro-6-(4-chlorophenyl)-5-[4-(methylthio)phenyl] pyrimidine;
2,4-Dichloro-5-(4-chlorophenyl)-6-(4-methylphenyl)pyrimidine;
4-Azido-5,6-diphenyl-2-(trifluoromethyl)pyrimidine;
4-Azido-6-[4-(methylsulfonyl)phenyl]-5-phenyl-2-(trifluoromethyl)pyrimidine;
4-Azido-5-(4-chlorophenyl)-6-[4-(methylsulfonyl)phenyl]-2-(trifluoromethyl)pyrimidine;
4-Azido-5-(4-fluorophenyl)-6-[4-(methylsulfonyl)phenyl]-2-(trifluoromethyl)pyrimidine;
2,4-Diazido-5,6-diphenylpyrimidine;
2,4-Diazido-5-(4-chlorophenyl)-6-phenylpyrimidine;
4-Hydrazino-5,6-diphenyl-2-(trifluoromethyl)pyrimidine;
4-Hydrazino-6-(4-methylphenyl)-5-phenyl-2-(trifluoromethyl)pyrimidine;
4-Hydrazino-6-(4-fluorophenyl)-5-phenyl-2-(trifluoromethyl)pyrimidine;
4-Hydrazino-6-[4-(methylsulfonyl)phenyl]-5-phenyl-2-(trifluoromethyl)pyrimidine;
5-(4-Chlorophenyl)-4-hydrazino-6-[4-(methylsulfonyl)phenyl]-2-(trifluoromethyl)pyrimidine;
5-(4-Fluorophenyl)-4-hydrazino-6-[4-(methylsulfonyl)phenyl]-2-(trifluoromethyl)pyrimidine;
2-Chloro-5,6-diphenyl-4-hydrazinopyrimidine;
2-Chloro-4-hydrazino-5-[4-(methylthio)phenyl]-6-phenylpyrimidine;
2,4-Dihydrazino-5,6-diphenylpyrimidine;
2,4-Dihydrazino-5-[4-(methylthio)phenyl]-6-phenylpyrimidine;
N'-[5,6-Diphenyl-2-(trifluoromethyl)pyrimidin-4-yl]acetohydrazide;
N'-[6-(4-Methylphenyl)-5-phenyl-2-(trifluoromethyl)pyrimidin-4-yl]acetohydrazide;
N'-[6-(4-Fluorophenyl)-5-phenyl-2-(trifluoromethyl)pyrimidin-4-yl]acetohydrazide;
N'-[6-[4-(Methylsulfonyl)phenyl]-5-phenyl-2-(trifluoromethyl)pyrimidin-4-yl]acetohydrazide;
N'-[5-(4-Chlorophenyl)-6-[4-(methylsulfonyl)phenyl]-2-(trifluoromethyl)pyrimidin-4-yl]acetohydrazide;
N'-[5-(6-Fluorophenyl)-6-[4-(methylsulfonyl)phenyl]-2-(trifluoromethyl)pyrimidin-4-yl]acetohydrazide;
N'-[5-(4-Chlorophenyl)-[6-(4-methylsulfonyl)phenyl]-2-(trifluoromethyl)pyrimidin-4-yl]trifluoroacetohydrazide;
4-Chloro-1,6-diphenylpyrimidine-2(1H)-one;
4-Azido-6-[(4-methylthio)phenyl]-1-phenylpyrimidin-2 (1H)-one;
4-[3-(4-Chlorophenyl)-2-oxo-6-trifluoromethyl-2,3-dihydro-pyrimidin-4-yl]benzenesulfonamide;
6-[(4-Methylsulfonyl)phenyl]-1-p-tolyl-4-(trifluoromethy) pyrimidin-2(1H)-one;
4-Azido-6-[(4-methylsulfonyl)phenyl]-1-p-tolyl-pyrimidin-2(1H)-one;
4-(6-Azido-3-methoxyphenyl-2-oxo-2,3-dihydropyrimidin-4-yl)benzenesulfonamide;
4-(6-Azido-4-methoxyphenyl-2-oxo-2,3-dihydropyrimidin-4-yl)benzenesulfonamide;
2-Chloro-5-(4-chlorophenyl)-4-methylthio-6-[(4-methylthio)phenyl]pyrimidine;
6-[(4-Methylthio)phenyl]-1-phenyl-4-(trifluoromethyl)pyrimidin-2(1H)-one;
4-(2-Oxo-3-phenyl-6-trifluoromethyl-2,3-dihydropyrimidin-4-yl)benzenesulfonamide;
4-Methylthio-5,6-bis(p-tolyl)pyrimidine;
4-Methylthio-5,6-diphenyl-pyrimidin-2-ol;
4-Methylsulfonyl-5,6-bis(p-tolyl)pyrimidine;
1,6-Diphenyl-4-(trifluoromethyl)pyrimidin-2(1H)-one;
4-(2-Hydroxy-6-methylthio-5-phenylpyrimidin-4-yl)benzenesulfonamide;
4-Methylthio-6-[(4-methylthio)phenyl]-5-phenylpyrimidine;.
2-Chloro-4-methylthio-5,6-bis(p-tolyl)pyrimidine;
2-Chloro-4-methylthio-6-[(4-methylthio)phenyl]-5-p-tolyl-pyrimidine;
5-(4-Bromophenyl)-2-chloro-4-methylthio-6-[(4-methylthio)phenyl]pyrimidine;
5-(2-Bromophenyl)-4-methylthio-6-[(4-methylthio)phenyl] pyrimidin-2-ol;
4-(2-Chloro-6-methylthio-5-phenylpyrimidin-4-yl)benzenesulfonamide;
2-Chloro-4,5-bis-(4-methoxyphenyl)-6-(methylthio)pyrimidine;
2-Chloro-4-methylthio-6-[(4-methylthio)phenyl]-5-phenylpyrimidine;
2,4-Diazido-6[(4-methylthio)phenyl)]-5-phenylpyrimidine;
2,4-Diazido-5-(4-bromophenyl)-6-(4-methylthiophenyl)pyrimidine;
4-Chloro-6-[(4-methylsulfonyl)phenyl]-1-phenylpyrimidin-2(1H)-one;
4-Azido-1-(2-fluorophenyl)-6-[(4-methylthio)phenyl]-pyrimidin-2(1H)-one;
2-[(4-Methylsulfonyl)phenyl]-6-trifluoromethyl-3-[(4-trifluoromethyl)phenyl]-3,4-dihydropyrimidin-4-ol;
5-(3-Fluorophenyl)-4-methylthio-6-[(4-methylthio)phenyl] pyrimidin-2-ol and
4-(6-Hydroxy-6-methyl-2-p-tolyl-4-trifluoromethyl-6H-pyrimidin-1-yl)benzenesulfonamide.

According to another embodiment of the present invention, there is provided a process for the preparation of novel compounds of the formula (I)

(I)

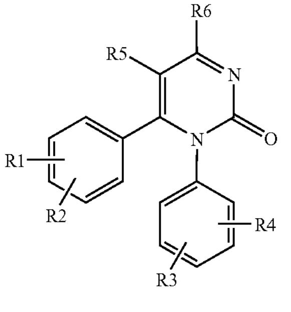

where all symbols are as defined earlier may be prepared by a process which comprises condensing a compound of formula (Ia)

(Ia)

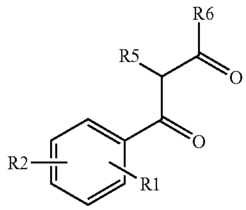

wherein all symbols are as defined earlier with a compound of the formula (Ib)

(Ib)

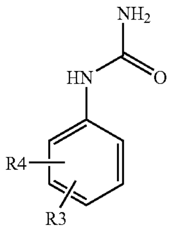

where all symbols are as defined above.

The reaction of compound of formula (Ia) with compound of formula (Ib) may be carried out using appropriate solvents like toluene, xylene, tetrahydrofuran, dioxane, chloroform, dichloromethane, dichloroethane, o-dichlorobenzene, acetone, ethylacetate, acetonitrile, N,N-dimethylformamide, dimethylsulfoxide, ethanol, methanol, isopropylalcohol, tert-butylalcohol, acetic acid, propionic acid etc., a mixture thereof or the like. The condensation reaction is carried out in acidic condition using mineral or organic acids, or basic conditions viz. carbonates, bicarbonates, hydrides, hydroxides, alkyls and alkoxides of alkali metals and alkaline earth metals or by neat reaction. The reaction is carried out using phase transfer catalysts viz. triethylbenzylammonium chloride, tetrabutylammonium bromide, tetrabutylammonium hydrogensulphate, tricaprylylmethylammonium chloride (aliquat 336) and the like. The reaction is usually carried out under cooling to refluxing conditions. The final product purified by using chromatographic techniques or by recrystallization.

According to another embodiment of the present invention, there is provided a process for the preparation of novel compounds of the formula (I)

(I)

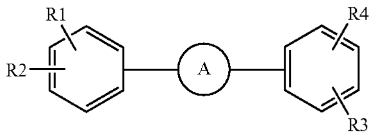

where A represents

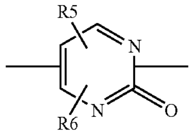

or

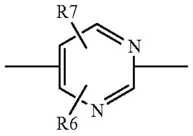

wherein $R^6$ represents halogen atom, $R^5$ and $R^7$ are as defined above may be prepared by converting the compound of formula (Ic)

(Ic)

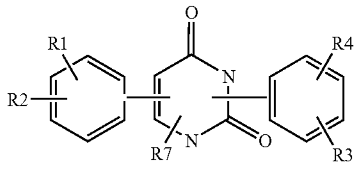

wherein all symbols are as defined earlier.

The compound of formula (Ic) is prepared according to the procedure described in our PCT application Nos. PCT/IB03/01287 and PCT/IB03/01289.

The conversion of compound of formula (Ic) is carried out using reagents such as phosphorus oxychloride, thionyl chloride, phosphorus trichloride, phosphorus pentachloride, oxalyl chloride and the like in the presence or absence of solvents such as toluene, xylene, tetrahydrofuran, dioxane, chloroform, dichloromethane, dichloroethane, o-dichlorobenzene, diphenyl ether and the like or a mixture thereof, in presence or absence of dimethylformamide, N,N-dimethylaniline, N,N-diethylaniline and the like. The reaction is carried out at a temperature in the range of 20° C. to reflux temperatures for a period in the range of 2 to 12 h.

In yet another embodiment of the present invention, there is provided a process for the preparation of novel compounds of the formula (I)

(I)

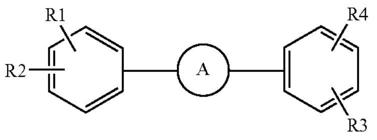

wherein A represents

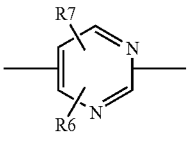

wherein any of $R^7$ represents halogen atom and $R^6$ is as defined earlier may be prepared by converting the compound of formula (Id)

(Id)

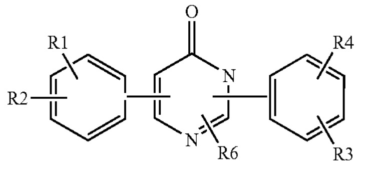

wherein $R^6$ is as defined earlier.

The compound of formula (Id) is prepared according to the procedure described in our PCT application No. PCT/IB03/01289.

The conversion of compound of formula (Id) is carried out using reagents such as phosphorusoxychloride, thionyl chloride, phosphorus trichloride, phosphorus pentachloride, oxalyl chloride and the like in the presence or absence of solvent such as toluene, xylene, tetrahydrofuran, dioxane, chloroform, dichloromethane, dichloroethane, o-dichlorobenzene, diphenyl ether and the like or a mixture thereof, in presence or absence of dimethylformamide, N,N-dimethylaniline, N,N-diethylaniline and the like. The reaction is carried out at a temperature in the range of 20° C. to reflux temperatures for a period in the range of 2 to 12 h.

In yet another embodiment of the present invention, there is provided a process for the preparation of novel compounds of the formula (I)

(I)

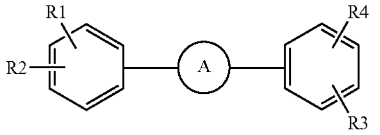

wherein A represents

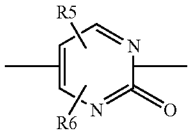

or

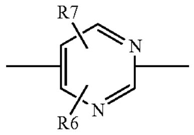

wherein $R^6$ represents azido, hydrazine or hydrazine derivatives, $R^5$ and $R^7$ are as defined above may be prepared by converting the compound of formula (Ie)

(Ie)

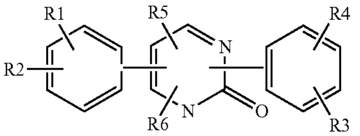

or (Ie)

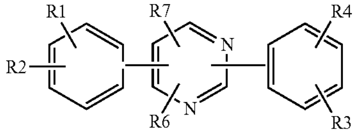

wherein $R^6$ represents halogen atom and all other symbols are as defined earlier.

The conversion of formula (Ie) may be carried out in the presence of one or more equivalents of metal azide such as $LiN_3$, $NaN_3$, trialkyl silylazide and the like or hydrazine hydrate or substituted hydrazine. The reaction may be carried out in the presence of solvent such as toluene, xylene, tetrahydrofuran, dioxane, chloroform, dichloromethane, dichloroethane, o-dichlorobenzene, acetone, ethylacetate, acetonitrile, N,N-dimethylformamide, dimethylsulfoxide, ethanol, methanol, isopropylalcohol, tert-butylalcohol, diphenyl ether and the like or a mixture thereof. The reaction may be carried out at a temperature in the range of ambient temperature to reflux temperature of the solvent, preferably at a temperature in the range of 80° C. to 100° C. The reaction time may range from 0.5 to 18 h.

In yet another embodiment of the present invention, there is provided a process for the preparation of novel compounds of the formula (I)

(I)

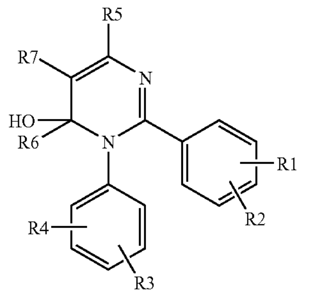

or (I)

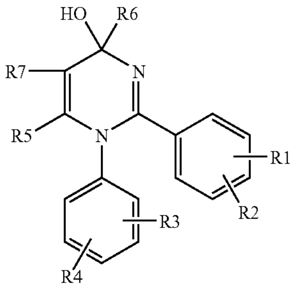

wherein all symbols are as defined earlier may be prepared by a process which comprises reacting a compound of the formula (If)

(If)

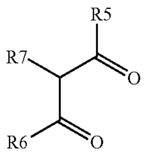

where all symbols are as defined earlier with a compound of formula (Ig)

(Ig)

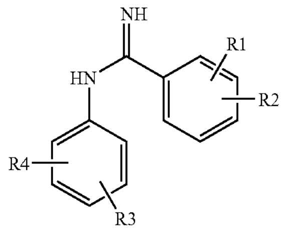

where all symbols are as defined earlier.

The reaction of compound of formula (If) with compound of formula (Ig) may be carried out using appropriate solvents like toluene, xylene, tetrahydrofuran, dioxane, chloroform, dichloromethane, dichloroethane, o-dichlorobenzene, acetone, ethylacetate, acetonitrile, N,N-dimethylformamide, dimethylsulfoxide, ethanol, methanol, isopropylalcohol, tert-butylalcohol, acetic acid, propionic acid, diphenyl ether etc., a mixture thereof or the like. The condensation reaction is carried out using acidic condition: mineral or organic acids, or basic conditions viz. carbonates, bicarbonates, hydrides, hydroxides, alkyls and alkoxides of alkali metals and alkaline earth metals or by neat reaction. The reaction is carried out using phase transfer catalysts viz. triethylbenzylammonium chloride, tetrabutylammonium bromide, tetrabutylammonium hydrogensulphate, tricaprylylmethylammonium chloride (aliquat 336) and the like. The reaction is carried out using polyphosphoric acid, phosphorus pentoxide, sulphuric acid and the like. The reaction is usually carried out under cooling to refluxing conditions. The final product is purified by using chromatographic techniques or by recrystallization.

According to yet another embodiment of the present invention, there is provided a process for the preparation of novel compounds of the formula (I)

(I)

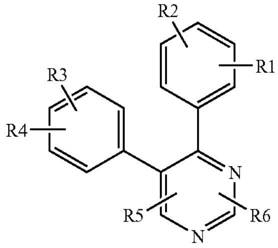

wherein all symbols are as defined earlier, which comprises i) reacting a compound of formula (Ih)

(Ih)

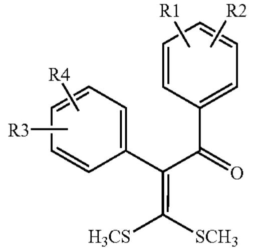

where all symbols are as defined earlier with a compound of formula (Ii)

(II)

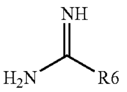

where $R^6$ is as defined earlier to produce compound of formula (Ij)

(Ij)

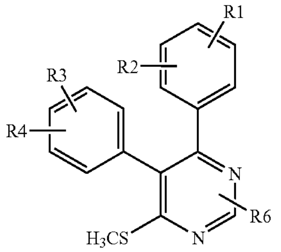

and ii) converting the compound of formula (Ij) to produce compound of formula (I) where all symbols are as defined earlier by reacting with suitable nucleophilic reagent.

The reaction of compound of formula (Ii) with compound of formula (Ij) may be carried out using appropriate solvents like toluene, xylene, tetrahydrofuran, dioxane, chloroform, dichloromethane, dichloroethane, o-dichlorobenzene, acetone, ethylacetate, acetonitrile, N,N-dimethylformamide, dimethylsulfoxide, ethanol, methanol, isopropylalcohol, tert-butylalcohol, acetic acid, propionic acid, diphenyl ether etc., a mixture thereof or the like. The condensation reaction is carried out using acidic condition: mineral or organic acids, or basic conditions viz. carbonates, bicarbonates, hydrides, hydroxides, alkyls and alkoxides of alkali metals and alkaline earth metals or by neat reaction. The reaction is carried out using phase transfer catalysts viz. triethylbenzylammonium chloride, tetrabutylammonium bromide, tetrabutylammonium hydrogensulphate, tricaprylylmethylammonium chloride (aliquat 336) and the like. The reaction is usually carried out under cooling to refluxing conditions. The final product is purified by using chromatographic techniques or by recrystallization.

The conversion of compound of formula (Ij) to compound of formula (I) may be carried out using conventional methods.

In yet another embodiment of the present invention, there is provided a process for the preparation of compounds of formula (I) wherein any of the groups $R_1$, $R_2$, $R_3$, $R_4$, $R_5$, $R_6$, $R_7$ represent hydrazine derivatives such as acylhydrazide may be prepared by reacting the compound of formula (I) wherein any of the groups $R_1$, $R_2$, $R_3$, $R_4$, $R_5$, $R_6$, $R_7$ represent hydrazine.

The reaction is carried out using reagents such as acetyl chloride, benzoyl chloride, acetic anhydride, trifluoroacetic anhydride, trichloroacetic anhydride and the like. The reaction may be carried out in the presence of solvent such as toluene, xylene, tetrahydrofuran, dioxane, chloroform, dichloromethane, dichloroethane, o-dichlorobenzene, acetonitrile, dimethylsulfoxide, diphenyl ether and the like or a mixture thereof in the presence of base such as carbonates, bicarbonates, hydrides, hydroxides, alkyls and alkoxides of alkali metals and alkaline earth metals; organic bases such as pyridine, triethyl amine and the like; acids like perchloric acid etc. The reaction may be carried out at a temperature in the range of ambient temperature to reflux temperature of the solvent.

According to yet another embodiment of the present invention there is provided a process for the conversion of novel compounds of the formula (I) wherein the groups $R_1$, $R_2$, $R_3$, $R_4$, $R_5$, $R_6$ represent alkylthio or arylthio to compounds of formula (I) wherein $R_1$, $R_2$, $R_3$, $R_4$, $R_5$, $R_6$ represent alkylsulfonyl, alkylsulfmyl, aryl sulfinyl or arylsulfonyl using suitable oxidising reagent. The oxidizing may be selected from potassium peroxymonosulfate (Oxone), hydrogen peroxide, tert-butylperoxide, Jones reagent, peracid [e.g peracetic acid, perbenzoic acid, m-chloroperbenzoic acid etc], chromic acid, potassium permanganate, alkali metal periodate [e.g sodium periodate, etc], magnesium mono peroxypthalate, osmium tetroxide/N-methylmorpholine-N-oxide, sodium tungstate, and the like. The oxidation is usually carried out in a solvent which does not adversely influence the reaction such as acetic acid, dichloromethane, acetone, ethyl acetate, chloroform, water, an alcohol [eg. methanol, ethanol, etc.], a mixture thereof or the like. The reaction is usually carried out under cooling to refluxing conditions.

According to yet another embodiment of the present invention there is provided a process for the conversion of novel compounds of the formula (I) wherein any of the groups $R_1$, $R_2$, $R_3$, $R_4$, $R_5$, $R_6$ represent alkylsulfonyl may be converted to compounds of the formula (I) wherein $R_1$, $R_2$, $R_3$, $R_4$, $R_5$, $R_6$ represent sulfamoyl group using the procedure described in the literature (Huang et. al. Tetrahedron Lett. 1994, 39, 7201).

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium isopropoxide, sodium hydride, potassium t-butoxide, calcium hydroxide, magnesium hydroxide and the like, in solvents like ether, tetrahydrofuran, methanol, t-butanol, dioxane, isopropanol, ethanol etc. Mixture of solvents may be used. Organic bases such as diethanolamine, α-phenylethylamine, benzylamine, piperidine, morpholine, pyridine, hydroxyethylpyrrolidine, hydroxyethylpiperidine, guanidine, choline and the like, ammonium or substituted ammonium salts, aluminum salts. Amino acid such as glycine, alanine, cystine, cysteine, lysine, arginine, phenylalanine, etc may be used for the preparation of amino acid salts. Alternatively, acid addition salts wherever applicable are prepared by the treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and in solvents like ethyl acetate, ether, alcohols, acetone, tetrahydrofuran, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolysing the pure diastereomeric amide.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

Pharmaceutically acceptable solvates of the compounds of formula (I) forming part of this invention may be prepared by conventional methods such as dissolving the compounds of formula (I) in solvents such as water, methanol, ethanol, mixture of solvents such as acetone:water, dioxane:water, N,N-dimethylformamide:water and the like, preferably water and recrystallizing by using different crystallization techniques.

The novel compounds of the present invention are useful for the treatment of inflammation and immunological diseases. Particularly the compound of the present invention are useful for the treatment of inflammation and immunological diseases those mediated by cytokines such as TNF-α, IL-1, IL-6, IL-1β, IL-8 and cyclooxygenase such as COX-1, COX-2 and COX-3. The compounds of the present invention are also useful for the treatment of rheumatoid arthritis; osteoporosis; multiple myeloma; uveititis; acute and chronic myelogenous leukemia; ischemic heart disease; atherosclerosis; cancer; ischemic-induced cell damage; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever and myalgias due to infection; and the diseases mediated by HIV-1; HIV-2; HIV-3; cytomegalovirus (CMV); influenza; adenovirus; the herpes viruses (including HSV-1, HSV-2) and herpes zoster viruses.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase.

The pharmaceutically active compounds of this invention can be processed in accordance with conventional methods of pharmacy to produce medicinal agents for administration to patients, including humans and other mammals.

The present invention provides a pharmaceutical composition, containing the compounds of the general formula (I) as defined above, their derivatives, their analogs, their tautomeric forms, their stereoisomers, their polymorphs, their pharmaceutically acceptable hydrates and solvates in combination with the usual pharmaceutically employed carriers, diluents and the like, useful for the treatment of arthritis, pain, fever, psoriasis, allergic diseases, asthma, inflammatory bowel syndrome, gastro-intestinal ulcers, cardiovascular disorders including ischemic heart disease, atherosclerosis, cancer, ischemic-induced cell damage, particularly brain damage caused by stroke, other pathological disorders associated with free radicals. The pharmaceutical composition of the present invention are effective in the treatment of inflammation and immunological diseases, particularly those mediated by cytokines such as TNF-α, IL-1, IL-6, IL-8 and cyclooxygenase such as COX-1, COX-2 and COX-3.

The pharmaceutical composition may be in the forms normally employed, such as tablets, capsules, powders, syrups, solutions, aerosols, suspensions and the like, may contain flavoring agents, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

The present invention is provided by the examples given below, which are provided by way of illustration only and should not be considered to limit the scope of the invention.

EXAMPLE 1

Synthesis of 4-chloro-5,6-diphenyl-2-(trifluoromethyl)pyrimidine

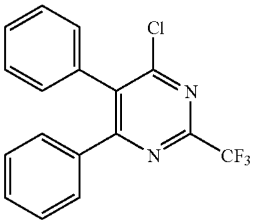

5,6-Diphenyl-2-(trifluoromethyl)pyrimidin-4(3H)-one (8.0 g, 25 mmol) (synthesized according to the procedure described in our PCT application No. IB03/01289) was refluxed in phosphorus oxychloride (15 ml) for 5 hours and allowed to cool to room temperature. The reaction mixture was poured onto ice-water mixture and neutralised with saturated sodium bicarbonate solution. The solid thus separated was extracted with dichloromethane. The organic extract was washed with water, dried over anhydrous sodium sulphate and concentrated under reduced pressure to give crude product, which was purified by column chromatography to afford the title compound (6.5 g, 76.6%, HPLC purity 99.8%), mp: 105-107° C.

$^1$H-NMR ($CDCl_3$): δ 7.19-7.41 (m, 10H). MS m/z: 335.1 ($M^+$).

EXAMPLE 2

Synthesis of 4-chloro-6-(4-methylphenyl)-5-phenyl-2-(trifluoromethyl)pyrimidine

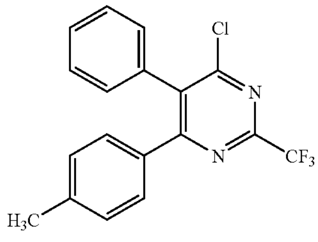

The title compound was prepared from 6-(4-methylphenyl)-5-phenyl-2-(trifluoromethyl)pyrimidin-4(3H)-one (1.4 g, 4.2 mmol) by following the procedure described in example 1 (0.68 g, 46%, HPLC purity 99.6%), mp: 97-100° C.

$^1$H-NMR ($CDCl_3$): δ 2.30 (s, 3H), 7.03-7.05 (d, 2H), 7.22-7.30 (m, 4H), 7.41-7.42 (m, 3H). MS m/z: 349.2 ($M^+$).

EXAMPLE 3

Synthesis of 4-chloro-6-(4-fluorophenyl)-5-phenyl-2-(trifluoromethyl)pyrimidine

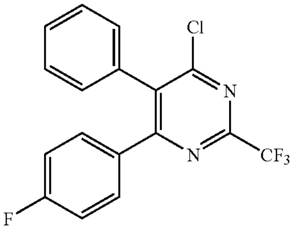

The title compound was prepared from 6-(4-fluorophenyl)-5-phenyl-2-(trifluoromethyl)pyrimidin-4(3H)-one (3.2 g, 9.57 mmol) by following the procedure described in example 1 (3.3 g, 97.7%, HPLC purity 99.5%), mp: 67-68° C.

$^1$H-NMR ($CDCl_3$): δ 6.90-6.95 (m, 2H), 7.19-7.26 (m, 2H), 7.39-7.44 (m, 5H). MS m/z: 353.2 ($M^+$).

EXAMPLE 4

Synthesis of 4-chloro-6-[4-(methylsulfonyl)phenyl]-5-phenyl-2-(trifluoromethyl)pyrimidine

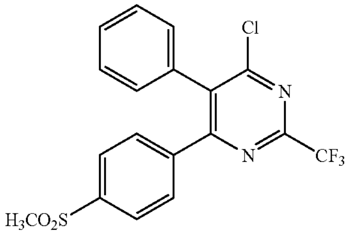

The title compound was prepared from 6-[4-(methylsulfonyl)phenyl]-5-phenyl-2-(trifluoromethyl)pyrimidin-4(3H)-one (3.3 g, 8.3 mmol) by following the procedure described in example 1 (2.6 g, 76%, HPLC purity 98.1% ), mp: 156-159° C.

$^1$H-NMR ($CDCl_3$): δ 3.02 (s, 3H), 7.18-7.21(d, 2H), 7.42-7.45 (m, 3H), 7.58 (d, 2H), 7.81-7.83 (d, 2H). MS m/z: 413.1($M^+$). IR (KBr) $cm^{-1}$: 1138 ($—SO_2—$).

EXAMPLE 5

Synthesis of 4-chloro-5-(4-chlorophenyl)-6-[4-(methylsulfonyl)phenyl]-2-(trifluoromethyl)pyrimidine

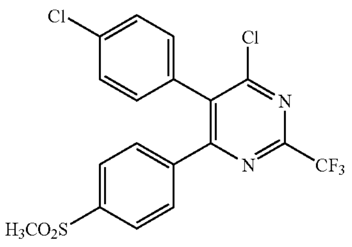

The title compound was prepared from 5-(4-chlorophenyl)-6-[4-(methylsulfonyl)phenyl]-2-(trifluoromethyl)pyrimidin- 4(3 H)-one (10.5 g, 24.4 mmol) by following the procedure described in example 1 (9.3 g, 85.32%, HPLC purity 98.92%), mp:188-190° C.

$^{1}$H-NMR ($CDCl_3$): δ 3.04 (s, 3H), 7.14-7.16 (d, 2H), 7.41-7.43 (d, 2H), 7.57-7.59 (d, 2H), 7.86-7.88 (d, 2H). IR (KBr) $cm^{-1}$: 1135 (—$SO_2$—).

EXAMPLE 6

Synthesis of 4-chloro-5-(4-fluorophenyl)-6-[4-(methylsulfonyl)phenyl]-2-(trifluoromethyl)pyrimidine

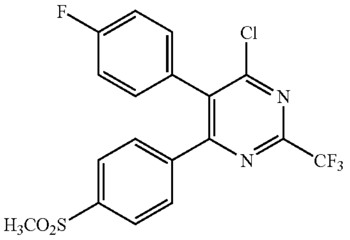

The title compound was prepared from 5-(4-fluorophenyl)-6-[4-(methylsulfonyl)phenyl]-2-(trifluoromethyl)pyrimidin-4(3H)-one (0.35 g, 0.85 mmol) by following the procedure described in example 1 (0.25 g, 68.4%, HPLC purity 99.6%), mp: 195-197° C.

$^{1}$H-NMR ($CDCl_3$): δ 3.04 (s, 3H), 7.11-7.21 (m, 4H), 7.56-7.58 (d, 2H), 7.85-7.87 (d, 2H). MS m/z: 431.2 ($M^+$). IR (KBr) $cm^{-1}$: 1136 (—$SO_2$—).

EXAMPLE 7

Synthesis of 2,4-dichloro-5,6-diphenylpyrimidine

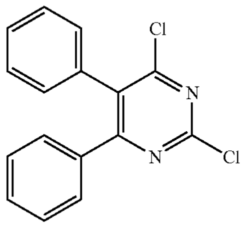

5,6-Diphenyl-uracil (0.21 g, 0.8mmol) was refluxed in phosphorus oxychloride (3 ml) for 3 hours and allowed to cool to room temperature. The reaction mixture was poured onto ice-water mixture and neutralised with saturated sodium bicarbonate solution. The solid thus separated was extracted with dichloromethane. The organic extract was washed with water, dried over anhydrous sodium sulphate and concentrated under reduced pressure to afford the title compound (0.08 g, 34%, HPLC purity 96.9%), mp: 144-146° C.

$^{1}$H-NMR ($CDCl_3$): δ 7.16-7.39 (m, 10H). MS m/z: 301.1 ($M^+$).

EXAMPLE 8

Synthesis of 2,4-dichloro-6-(4-methylphenyl)-5-phenylpyrimidine

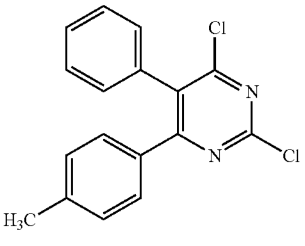

The title compound was prepared from 6-(4-methylphenyl)-5-phenyl-uracil (0.87 g, 3.1 mmol) by following the procedure described in example 7(0.38 g, 38.6%, HPLC purity 100%), mp: 130-132° C.

$^{1}$H-NMR ($CDCl_3$): δ 2.29 (s, 3H), 7.01-7.17 (d, 2H), 7.19-7.26 (m, 4H), 7.38-7.40 (d, 3H). MS m/z: 316.8 ($M^+$).

EXAMPLE 9

Synthesis of 6-(4-chlorophenyl)-2,4-dichloro-5-phenylpyrimidine

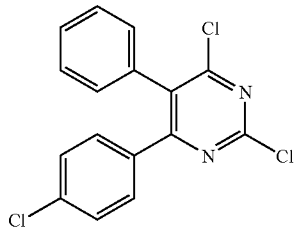

The title compound was prepared from 6-(4-chlorophenyl)-5-phenyl-uracil (0.4 g, 1.33 mmol) by following the procedure described in example 7 (0.28 g, 62.4%, HPLC purity 98.4%), mp: 129-131° C.

$^{1}$H-NMR ($CDCl_3$): δ 7.15-7.21 (m, 4H), 7.28-7.39 (m, 2H), 7.40-7.41 (m, 3H). MS m/z: 336.9 ($M^+$).

EXAMPLE 10

Synthesis of 5-(4-chlorophenyl)-2,4-dichloro-6-phenylpyrimidine

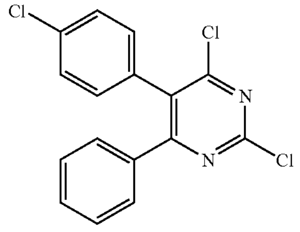

The title compound was prepared from 5-(4-chlorophenyl)-6-phenyl-uracil (0.59 g, 2 mmol) by following the procedure described in example 7 (0.43 g, 65.2%, HPLC purity 100%), mp: 123-125° C.

$^{1}$H-NMR ($CDCl_3$): δ 7.10-7.13 (d, 2H), 7.24-7.36 (m, 7H). MS m/z: 336.9 ($M^+$).

EXAMPLE 11

Synthesis of 2,4-dichloro-5-(4-methoxyphenyl)-6-phenylpyrimidine

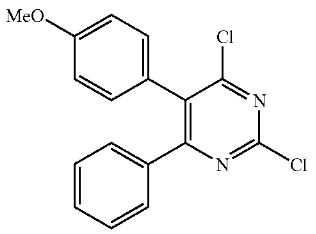

The title compound was prepared from 5-(4-methoxyphenyl)-6-phenyl-uracil (1.5 g, 5.1 mmol) by following the procedure described in example 7 (1 g, 59.2%, HPLC purity 99.4%), mp: 132-134° C.

$^1$H-NMR ($CDCl_3$): δ 3.82 (s, 3H), 6.87-6.9 (d, 2H), 7.07-7.09 (d, 2H), 7.26-7.36 (m, 5H). MS m/z: 332.9 ($M^+$).

EXAMPLE 12

Synthesis of 2,4-dichloro-5-[4-(methylthio)phenyl]-6-phenylpyrimidine

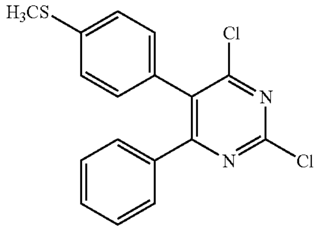

The title compound was prepared from 5-[4-(methylthio) phenyl]-6-phenyl-uracil (0.28 g, 2.6 mmol) by following the procedure described in example 7 (0.22 g, 68.6%, HPLC purity 100%), mp: 88-90° C.

$^1$H-NMR ($CDCl_3$): δ 2.49 (s, 3H), 7.06-7.08 (d, 2H), 7.2-7.36 (m, 7H). MS m/z: 349 ($M^+$).

EXAMPLE 13

Synthesis of 2,4-dichloro-6-(4-chlorophenyl)-5-[4-(methylthio)phenyl]pyrimidine

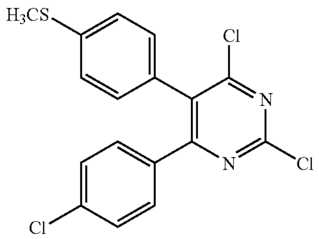

The title compound was prepared from 6-(4-chlorophenyl)-5-[4-(methylthio)phenyl]uracil (0.4 g, 1.1 mmol) by following the procedure described in example 7 (0.23 g, 52%, HPLC purity 99.7%), mp: 144-146° C. $^1$H-NMR ($CDCl_3$): δ 2.51 (s, 3H), 7.06-7.08 (d, 2H), 7.21-7.29 (m, 4H), 7.30-7.32 (d, 2H). MS m/z: 381.9 ($M^+$).

EXAMPLE 14

Synthesis of 2,4-dichloro-5-(4-chlorophenyl)-6-(4-methylphenyl)pyrimidine

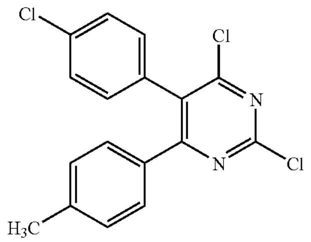

The title compound was prepared from 5-(4-chlorophenyl)-6-(4-methylphenyl)uracil (0.34 g, 1.1 mmol) by following the procedure described in example 7 (0.25 g, 65.8%, HPLC purity 97.6%), mp: 223-225° C.

$^1$H-NMR (DMSO-$d_6$): δ 2.26 (s, 3H), 7.10-7.12 (d, 2H), 7.19-7.21 (d, 2H), 7.32-7.34 (d, 2H), 7.47-7.57 (d, 2H). MS m/z: 350.9 ($M^+$).

EXAMPLE 15

Synthesis of 4-azido-5,6-diphenyl-2-(trifluoromethyl)pyrimidine

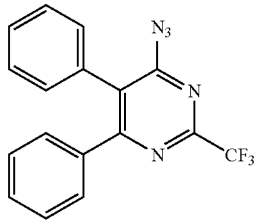

4-Chloro-5,6-diphenyl-2-(trifluoromethyl)pyrimidine (0.5 g, 1.5 mmol) (synthesized according to the procedure described in example 1) was refluxed in ethanol (10 ml) containing sodium azide (0.1 g, 1.5 mmol) for 8 hours and allowed to cool to room temperature. The reaction mixture was poured onto ice-water mixture. The solid thus separated was extracted with ethyl acetate. The organic extract was washed with water, dried over anhydrous sodium sulphate and concentrated under reduced pressure to afford the title compound (0.45 g, 88.3%, HPLC purity 98.5%), mp: 126-128° C.

$^1$H-NMR ($CDCl_3$): δ 7.15-7.17 (d, 2H), 7.23-7.38 (m, 8H). MS m/z: 342.1($M^+$).

EXAMPLE 16

Synthesis of 4-azido-6-[4-(methylsulfonyl)phenyl]-5-phenyl-2-(trifluoromethyl)pyrimidine

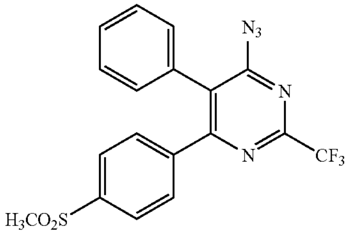

The title compound was prepared from 4-chloro-6-[4-(methylsulfonyl)phenyl]-5-phenyl-2-(trifluoromethyl)pyrimidine (0.5 g, 1.2 mmol) (synthesized according to the procedure described in example 4) by following the procedure described in example 15 (0.38 g, 74.2%, HPLC purity 98%), mp: 172-175° C.

$^1$H-NMR (DMSO-$d_6$): δ 3.21 (s, 3H), 7.27-7.3(d, 2H), 7.38-7.39 (d, 3H), 7.54-7.56 (d, 2H), 7.84-7.86 (d, 2H). MS m/z: 420.1($M^+$). IR (KBr) $cm^{-1}$: 1151 (—$SO_2$—).

EXAMPLE 17

Synthesis of 4-azido-5-(4-chlorophenyl)-6-[4-(methylsulfonyl)phenyl]-2-(trifluoromethyl)pyrimidine

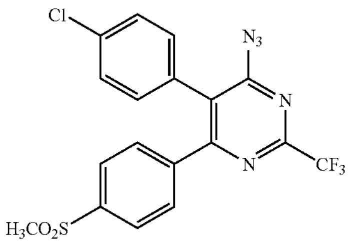

The title compound was prepared from 4-chloro-5-(4-chlorophenyl)-6-[4-(methylsulfonyl)phenyl]-2-(trifluoromethyl) pyrimidine (0.75 g, 1.68 mmol) (synthesized according to the procedure described in example 5) by following the procedure described in example 15 (0.6 g, 79%, HPLC purity 99%), mp: 317-320° C.

$^1$H-NMR ($CDCl_3$): δ 3.03(s, 3H), 7.08-7.10 (d, 2H), 7.36-7.38 (d, 2H), 7.56-7.58 (d, 2H), 7.85-7.87 (d, 2H). MS m/z: 454 ($M^+$). IR (KBr) $cm^{-1}$: 1148 (—$SO_2$—).

EXAMPLE 18

Synthesis of 4-azido-5-(4-fluorophenyl)-6-[4-(methylsulfonyl)phenyl]-2-(trifluoromethyl)pyrimidine

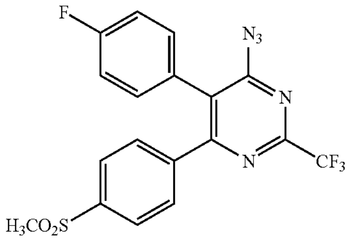

The title compound was prepared from 4-chloro-5-(4-fluorophenyl)-6-[4-(methylsulfonyl)phenyl]-2-(trifluoromethyl) pyrimidine (0.75 g, 1.74 mmol) (synthesized according to the procedure described in example 6) by following the procedure described in example 15 (0.53 g, 70%, HPLC purity 99.38%), mp:285-288° C.

$^1$H-NMR ($CDCl_3$): δ 3.03(s, 3H), 7.06-7.15 (m, 4H), 7.55-7.57 (d, 2H), 7.84-7.86 (d, 2H). MS m/z: 438.1($M^+$). IR (KBr) $cm^{-1}$: 1149 (—$SO_2$—).

EXAMPLE 19

Synthesis of 2,4-Diazido-5,6-diphenylpyrimidine

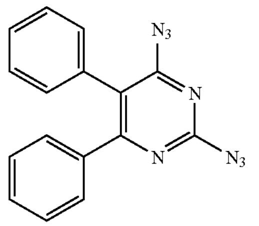

2,4-Dichloro-5,6-diphenylpyrimidine (0.5 g, 1.7 mmol) (synthesized according to the procedure described for example 7) was refluxed with sodium azide (0.24 g, 3.65 mmol) in ethanol (10 ml) under stirring for 8 hours. The reaction mixture was poured onto ice-water mixture. The solid thus separated was extracted with ethyl acetate. The organic extract was washed with water, dried over anhydrous sodium sulphate and concentrated under reduced pressure to give crude product, which was purified by column chromatography to afford the title compound (0.21 g, 40.8%), mp: 132-136° C.

$^1$H-NMR ($CDCl_3$): δ 7.10-7.11(m, 2H), 7.20-7.22 (m, 2H), 7.25-7.35 (m, 6H). MS m/z: 315.1 ($M^+$).

EXAMPLE 20

Synthesis of 2,4-diazido-5-(4-chlorophenyl)-6-phenylpyrimidine

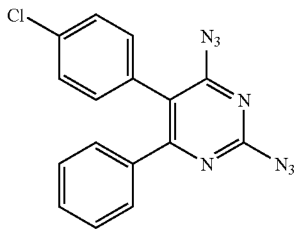

The title compound was prepared from 2,4-dichloro-5-(4-chlorophenyl)-6-phenylpyrimidine (0.3 g, 0.89 mmol) (obtained according to the procedure described in example 10) by following the procedure described in example 19 (0.15 g, 48.2%), mp: 105-109° C.

$^1$H-NMR ($CDCl_3$): δ 7.04-7.07 (d, 2H), 7.24-7.34 (m, 7H). MS m/z: 349.1 ($M^+$).

EXAMPLE 21

Synthesis of 4-hydrazino-5,6-diphenyl-2-(trifluoromethyl)pyrimidine

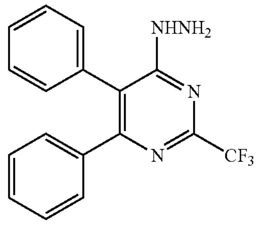

4-Chloro-5,6-diphenyl-2-(trifluoromethyl)pyrimidine (1.8 g, 5.3 mmol) (synthesized according to the procedure described in example 1) was stirred in ethanol (10 ml) containing hydrazine hydrate (0.64 g, 12.8 mmol) for 2 hours at 35° C. The crystals thus obtained in the reaction mixture was filtered under vacuum, washed with ethanol (5 ml) and dried to yield the title compound (1.7 g, 95.7%, HPLC purity 99.2%), mp: 182-186° C.

$^1$H-NMR ($CDCl_3$): δ 4.0 (bs, 2H, $D_2O$ exchangeable), 6.20 (s, 1H, $D_2O$ exchangeable), 7.15-7.41 (m, 10H). MS m/z: 331.2 ($M^+$). IR (KBr) $cm^{-1}$: 3328, 3271, 3029 (—NH—).

EXAMPLE 22

Synthesis of 4-hydrazino-6-(4-methylphenyl)-5-phenyl-2-(trifluoromethyl)pyrimidine

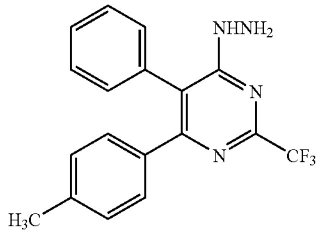

The title compound was prepared from 4-chloro-6-(4-methylphenyl)-5-phenyl-2-(trifluoromethyl)pyrimidine (0.55 g, 1.6 mmol) (synthesized according to the procedure described in example 2) by following the procedure described in example 21 (0.54 g, 99.4%, HPLC purity 99.7%), mp: 188-191° C.

$^1$H-NMR ($CDCl_3$): δ 2.27 (s, 3H), 4.0 (bs, 1H, $D_2O$ exchangeable), 6.2 (s, 1H, $D_2O$ exchangeable), 6.98-7.0 (d, 2H), 7.15-7.18 (d, 2H), 7.22-7.26 (m, 3H), 7.4-7.42 (m, 3H). MS m/z: 345.2 ($M^+$). IR (KBr) $cm^{-1}$: 3313, 3203, 3046 (—NH—).

EXAMPLE 23

Synthesis of 4-hydrazino-6-(4-fluorophenyl)-5-phenyl-2-(trifluoromethyl)pyrimidine

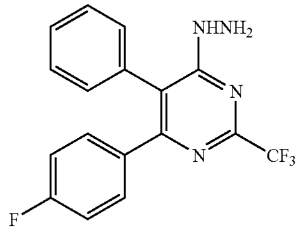

The title compound was prepared from 4-chloro-6-(4-fluorophenyl)-5-phenyl-2-(trifluoromethyl)pyrimidine (2.8 g, 7.9 mmol) (synthesized according to the procedure described in example 3) by following the procedure described in example 21 (2.3 g, 83.3%, HPLC purity 99.4%), mp: 175-177° C.

$^1$H-NMR ($CDCl_3$): δ 4.0 (bs, 2H, $D_2O$ exchangeable), 6.2 (s, 1H, $D_2O$ exchangeable), 6.85-6.90 (m, 2H), 7.14-7.16 (m, 2H), 7.32-7.43 (m, 5H). MS m/z: 349.2 ($M^+$). IR (KBr) $cm^{-1}$: 3327, 3270 (—NH—).

EXAMPLE 24

Synthesis of 4-hydrazino-6-[4-(methylsulfonyl)phenyl]-5-phenyl-2-(trifluoromethyl)pyrimidine

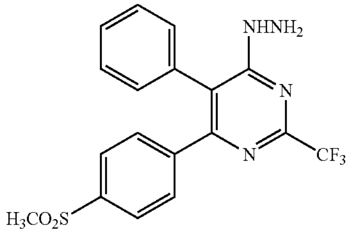

The title compound was prepared from 4-chloro-6-[4-(methylsulfonyl)phenyl]-5-phenyl-2-(trifluoromethyl)pyrimidine (0.41 g, 1 mmol) (synthesized according to the procedure described in example 4) by following the procedure described in example 21 (0.37 g, 91.1%, HPLC purity 97.5%), mp: 272-275° C.

$^1$H-NMR ($CDCl_3$): δ 2.99 (s, 3H), 4.09 (bs, 2H, $D_2O$ exchangeable), 6.31 (s, 1H, $D_2O$ exchangeable), 7.14-7.16 (d, 2H), 7.42-7.43 (d, 3H), 7.52-7.54 (d, 2H), 7.76-7.78 (d, 2H). MS m/z: 408.41 ($M^+$). IR (KBr) $cm^{-1}$: 3330, 3246 (—NH—), 1149 (—$SO_2$—).

EXAMPLE 25

Synthesis of 5-(4-chlorophenyl)-4-hydrazino-6-[4-(methylsulfonyl)phenyl]-2-(trifluoromethyl)pyrimidine

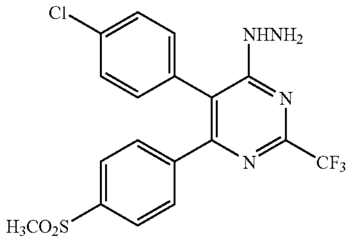

The title compound was prepared from 4-chloro-5-(4-chlorophenyl)-6-[4-(methylsulfonyl)phenyl]-2-(trifluoromethyl) pyrimidine (5.9 g, 13.2 mmol) (synthesized according to the procedure described in example 5) by following the procedure described in example 21 (5.11 g, 87.5%, HPLC purity 99.51%), mp: 266-269° C.

$^1$H-NMR ($CDCl_3$): δ 3.01 (s, 3H), 4.0 (bs, 2H, $D_2O$ exchangeable), 6.25 (s, 1H, $D_2O$ exchangeable), 7.09-7.11 (d, 2H), 7.42-7.44 (d, 2H), 7.50-7.53 (d, 2H), 7.80-7.82 (d, 2H). MS m/z: 443.1 ($M^+$). IR (KBr) $cm^{-1}$: 3333, 3235 (—NH—), 1144(—$SO_2$—).

EXAMPLE 26

Synthesis of 5-(4-fluorophenyl)-4-hydrazino-6-[4-(methylsulfonyl)phenyl]-2-(trifluoromethyl)pyrimidine

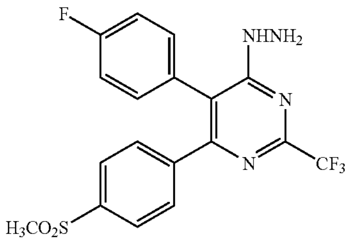

The title compound was prepared from 4-chloro-5-(4-fluorophenyl)-6-[4-(methylsulfonyl)phenyl]-2-(trifluoromethyl)pyrimidine (0.4 g, 0.93 mmol) (synthesized according to the procedure described in example 6) by following the procedure described in example 21 (0.25 g, 63%, HPLC purity 97.7%), mp: 286-290° C.

$^1$H-NMR (DMSO-$d_6$): δ 3.18 (s, 3H), 4.54 (bs, 2H, $D_2O$ exchangeable), 7.21-7.25 (m, 4H), 7.45-7.47 (d, 2H), 7.78-7.80 (d, 2H), 8.2 (s, 1H, $D_2O$ exchangeable). MS m/z: 427.1 ($M^+$). IR (KBr) $cm^{-1}$: 3327, 3242 (—NH—), 1149 (—$SO_2$—).

EXAMPLE 27

Synthesis of 2-chloro-5,6-diphenyl-4-hydrazinopyrimidine

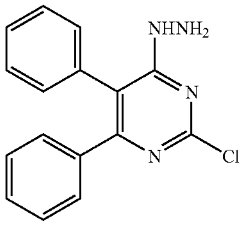

2,4-Dichloro-5,6-diphenylpyrimidine (2.0 g, 6.6 mmol) (synthesized according to the procedure described in example 7) was treated with hydrazine hydrate (0.73 g, 14.6 mmol) in ethanol (10 ml) under stirring for 5 hours at room temperature. The reaction mixture was poured onto ice-water mixture. The solid thus separated was extracted with diethylether. The organic extract was washed with water, dried over anhydrous sodium sulphate and concentrated under reduced pressure to afford the title compound (0.64 g, 32.5%).

$^1$H-NMR ($CDCl_3$): δ 4.0 (bs, 2H, $D_2O$ exchangeable), 6.2 (s, 1H, $D_2O$ exchangeable), 7.12-7.38 (m, 10H). MS m/z: 297.3 ($M^+$).

EXAMPLE 28

Synthesis of 2-chloro-4-hydrazino-5-[4-(methylthio)phenyl]-6-phenylpyrimidine

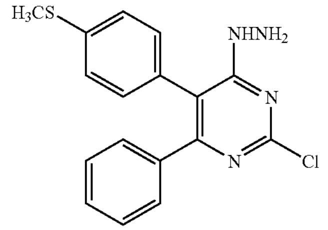

The title compound was prepared from 2,4-dichloro-5-[4-(methylthio)phenyl]-6-phenylpyrimidine (1.0 g, 2.9 mmol) (obtained according to the procedure described in example 12) by following the procedure described in example 27 (0.33 g, 33.4%, HPLC purity 98.6%), mp: 272-274° C.

$^1$H-NMR ($CDCl_3$): δ 2.48 (s, 3H), 3.99 (bs, 2H, $D_2O$ exchangeable), 6.15 (s, 1H, $D_2O$ exchangeable), 7.02-7.04 (d, 2H), 7.19-7.31 (m, 7H). MS m/z: 343.1 ($M^+$). IR (KBr) $cm^{-1}$: 3272 (—NH—).

EXAMPLE 29

Synthesis of 2,4-dihydrazino-5,6-diphenylpyrimidine

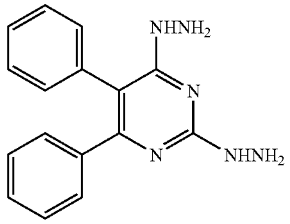

2,4-Dichloro-5,6-diphenylpyrimidine (0.5 g, 1.7 mmol) (synthesized according to the procedure described in example 7) was refluxed with hydrazine hydrate (0.18 g, 3.6 mmol) in ethanol (10 ml) under stirring for 6 hours. The reaction mixture was poured onto ice-water mixture. The solid thus separated was extracted with dichloromethane. The organic extract was washed with water, dried over anhydrous sodium sulphate and concentrated under reduced pressure to afford the title compound (0.12 g, 25%).

$^1$H-NMR ($CDCl_3$): δ 3.96 (bs, 3H, $D_2O$ exchangeable), 5.93 (s, 1H, $D_2O$ exchangeable), 6.34 (s, 1H, $D_2O$ exchangeable), 7.08-7.18 (m, 5H), 7.28-7.32 (m, 5H). MS m/z: 293.2 ($M^+$).

EXAMPLE 30

Synthesis of 2,4-dihydrazino-5-[4-(methylthio)phenyl]-6-phenylpyrimidine

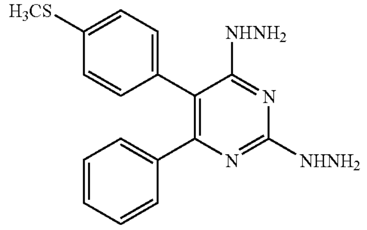

The title compound was prepared from 2,4-dichloro-5-[4-(methylthio)phenyl]-6-phenylpyrimidine (0.32 g, 0.93 mmol) (synthesized according to the procedure described in example 12) by following the procedure described in example 29 (0.26 g, 81.2%, HPLC purity 95.8%), mp: 207-210° C.

$^1$H-NMR ($CDCl_3$): δ 2.46 (s, 3H), 4.0 (bs, 4H, $D_2O$ exchangeable), 5.91 (s, 1H, $D_2O$ exchangeable), 6.35 (s, 1H, $D_2O$ exchangeable), 7.0-7.02 (d, 2H), 7.16-7.31 (m, 7H). MS m/z: 339.2 (M). IR (KBr) $cm^{-1}$: 3308, 3257 (—NH—).

EXAMPLE 31

Synthesis of N'-[5,6-diphenyl-2-(trifluoromethyl) pyrimidin-4-yl]acetohydrazide

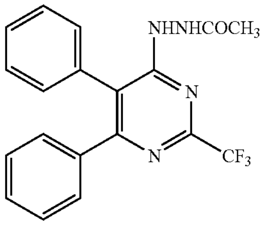

4-Hydrazino-5,6-diphenyl-2-(trifluoromethyl)pyrimidine (0.7 g, 2.1 mmol) (synthesized according to the procedure described in example 21) in pyridine (10 ml) was added acetylchloride (0.17 g, 2.2 mmol) dropwise at 20° C. under stirring for 10 minutes. After 30 minutes of stirring, the reaction mixture was poured onto ice-water mixture, acidified to pH 4 using hydrochloric acid and extracted with ethyl acetate. The organic extract was washed with water, dried over anhydrous sodium sulphate and concentrated under reduced pressure to afford the crude product, which was purified by column chromatography to furnish the title compound (0.2 g, 25.4%, HPLC purity 99.4%), mp: 113-116° C.

$^1$H-NMR ($CDCl_3$): δ 2.12 (s, 3H), 7.19-7.22 (m, 3H, 1H is $D_2O$ exchangeable), 7.26-7.45 (m, 8H), 8.0-8.2 (s, 1H, $D_2O$ exchangeable). MS m/z: 373.2 ($M^+$). IR (KBr) $cm^{-1}$: 3330, 3268 (—NH—), 1686 (—C═O).

EXAMPLE 32

Synthesis of N'-[6-(4-methylphenyl)-5-phenyl-2-(trifluoromethyl)pyrimidin-4-yl]acetohydrazide

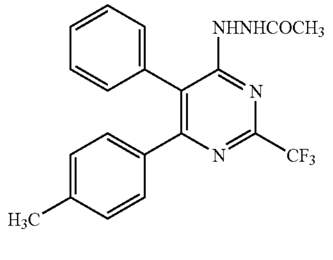

To a solution of 4-hydrazino-6-(4-methylphenyl)-5-phenyl-2-(trifluoromethyl)pyrimidine (0.23 g, 0.66 mmol) (synthesized according to the procedure described in example 22) in dichloromethane (5 ml) and pyridine (0.06 g, 0.8 mmol), acetyl chloride (0.6 g, 0.7 mmol) was added dropwise at room temperature over a period of ten minutes under stirring. Stirring was continued for two hours and the resultant reaction mass was poured onto ice-water mixture and neutralised with hydrochloric acid. The reaction mixture was extracted with dichloromethane. The organic extract was washed with water, dried over anhydrous sodium sulphate and concentrated under reduced pressure to afford the title compound (0.2 g, 77.9%, HPLC purity 99.4%), mp: 147-152° C.

$^1$H-NMR. ($CDCl_3$): δ 2.11 (s, 3H), 2.27 (s, 3H), 6.99-7.01 (d, 2H), 7.22-7.28 (m, 5H, 1H is $D_2O$ exchangeable), 7.42-7.44 (m, 3H), 8.0 (d, 1H, $D_2O$ exchangeable). MS m/z: 387.2 ($M^+$). IR (KBr) $cm^{-1}$: 3287(—NH—), 1670 (—C═O).

EXAMPLE 33

Synthesis of N'-[6-(4-fluorophenyl)-5-phenyl-2-(trifluoromethyl)pyrimidin-4-yl]acetohydrazide

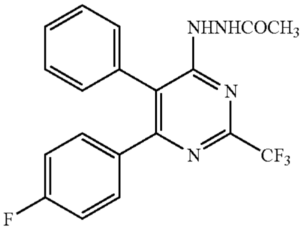

The title compound was prepared from 4-hydrazino-6-(4-fluorophenyl)-5-phenyl-2-(trifluoromethyl)pyrimidine (0.8 g, 2.3 mmol) (synthesized according to the procedure described in example 23) by following the procedure described in example 32 (0.84 g, 93.5%, HPLC purity 97.9%), mp: 149-153° C.

$^1$H-NMR ($CDCl_3$): δ 2.1 (s, 3H), 6.87-6.91 (m, 2H), 7.26-7.27 (m, 1H, $D_2O$ exchangeable), 7.32-7.46 (m, 7H), 8.0 (d, 1H, $D_2O$ exchangeable). MS m/z: 391.1 ($M^+$). IR (KBr) $cm^{-1}$: 3376, 3261 (—NH—), 1669 (—C═O).

EXAMPLE 34

Synthesis of N'-[6-[4-(methylsulfonyl)phenyl]-5-phenyl-2-(trifluoromethyl)pyrimidin-4-yl]acetohydrazide

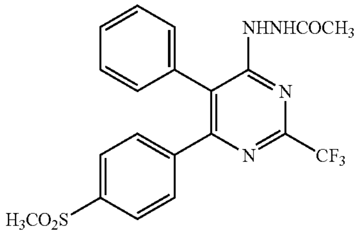

The title compound was prepared from 4-hydrazino-6-[4-(methylsulfonyl)phenyl]-5-phenyl-2-(trifluoromethyl)pyrimidine (0.45 g, 1.1 mmol) (synthesized according to the procedure described in example in 24) by following the procedure described in example 32 (0.29 g, 58.5%, HPLC purity 99.6%), mp: 265-268° C.

$^1$H-NMR ($CDCl_3$): δ 1.9 (s, 3H), 3.18 (s, 3H), 7.24-7.26 (d, 2H), 7.39-7.48 (m, 5H), 7.76-7.86 (d, 2H), 8.7 (s, 1H, $D_2O$ exchangeable), 10 (s, 1H, $D_2O$ exchangeable). MS m/z: 451.2 ($M^+$). IR (KBr) $cm^{-1}$: 3331 (—NH—), 1693 (—C═O), 1148(—$SO_2$—).

EXAMPLE 35

Synthesis of N'-[5-(4-chlorophenyl)-6-[4-(methylsulfonyl)phenyl]-2-(trifluoromethyl)pyrimidin-4-yl] acetohydrazide

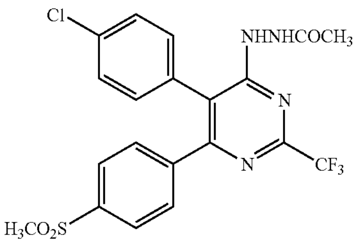

The title compound was prepared from 5-(4-chlorophenyl)-4-hydrazino-6-[4-(methylsulfonyl)phenyl]-2-(trifluoromethyl)pyrimidine (1.0 g, 2.2 mmol) (synthesized according to the procedure described in example 25) by following the procedure described in example 32 (0.8 g, 73.2%, HPLC purity 99.8%), mp: 254-256° C.

$^1$H-NMR (DMSO-$d_6$): δ 1.9 (s, 3H), 3.2 (s, 3H), 7.27-7.29 (m, 2H), 7.46-7.51 (m, 4H), 7.81-7.83, (d, 2H), 8.75 (s, 1H, $D_2O$ exchangeable), 10 (s, 1H, $D_2O$ exchangeable). MS m/z: 485.2 ($M^+$). IR (KBr) $cm^{-1}$: 3317 (—NH—), 1695 (—C═O), 1152 (—$SO_2$).

EXAMPLE 36

Synthesis of N'-[5-(6-fluorophenyl)-6-[4-(methylsulfonyl)phenyl]-2-(trifluoromethyl)pyrimidin-4-yl] acetohydrazide

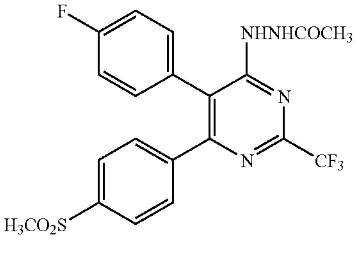

The title compound was prepared from 5-(4-fluorophenyl)-4-hydrazino-6-[4-(methylsulfonyl)phenyl]-2-(trifluoromethyl)pyrimidine (0.75 g, 1.7 mmol) (synthesized according to the procedure described in example 26) by following the procedure described in example 32 (0.7 g, 83.7%, HPLC purity 98.4%), mp: 281-283° C.

$^1$H-NMR (DMSO-$d_6$): δ 1.9 (s, 3H), 3.2 (s, 3H), 7.24-7.30 (m, 2H), 7.48-7.50 (m, 4H), 7.80-7.82 (d, 2H), 8.75 (s, 1H, $D_2O$ exchangeable), 10 (s, 1H, $D_2O$ exchangeable). MS m/z: 469.1 ($M^+$). IR (KBr) $cm^{-1}$: 3381, 3325 (—NH—), 1694 (—C═O), 1146 (—$SO_2$).

EXAMPLE 37

Synthesis of N'-[5-(4-chlorophenyl)-[6-(4-methylsulfonyl)phenyl]-2-(trifluoromethyl)pyrimidin-4-yl] trifluoroacetohydrazide

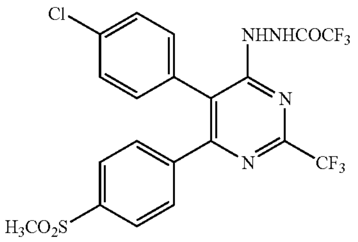

To a solution of 5-(4-chlorophenyl)-4-hydrazino-6-[4-(methylsulfonyl)phenyl]-2-(trifluoromethyl)pyrimidine (0.5 g, 1.1 mmol) (synthesized according to the procedure described in example 25) in dichloromethane (5 ml) and pyridine (0.1 g, 1.2 mmol), trifluoroacetic anhydride (0.24 g, 1.2 mmol) was added dropwise at 0° C. to 10° C. over a period of ten minutes under stirring. Stirring was continued for 0.5 hr and the resultant reaction mass was poured onto ice-water mixture and extracted with dichloromethane. The organic extract was washed with water, dried over anhydrous sodium sulphate and concentrated under reduced pressure to afford the title compound (0.3 g, 49.3%, HPLC purity 97.6%), mp: 307-309° C.

$^1$H-NMR (DMSO-$d_6$): δ 3.21 (s, 3H), 7.32-7.34 (d, 2H), 7.5-7.55 (m, 4H), 7.83-7.85 (d, 2H), 9.3 (s, 1H, $D_2O$ exchangeable), 11.75 (s, 1H, $D_2O$ exchangeable). MS m/z: 539.2 ($M^+$). IR (KBr) $cm^{-1}$: 3404, 3255 (—NH—), 1762 (—C═O), 1153 (—$SO_2$).

EXAMPLE 38

Synthesis of 4-chloro-1,6-diphenylpyrimidine-2(1H)-one

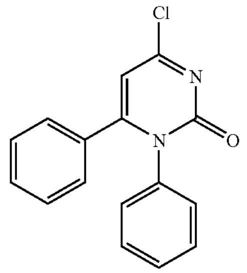

Oxalyl chloride (3.1 g, 24.4 mmol) was added to a mixture of N,N-dimethylformamide (1.8 g, 24.6 mmol) in dichloromethane (30 ml) at −5° C. to 0° C. under stirring. After the completion of addition the reaction temperature was allowed to reach 20° C. to 25° C. 1,6-Diphenyluracil (4.0 g, 15.2 mmol) was added in portions to the resulted suspension for 2.5 hrs. The reaction mixture was heated to reflux for 4 hours under stirring and continued stirring for 12 hours at room temperature. The reaction mass was poured onto sodium hydroxide solution (150 ml, 0.25 N) and collected the dichloromethane layer. The dichloromethane layer was washed with hydrochloric acid (200 ml, 0.025N), water and saturated sodium chloride solution successively. The organic extract was dried over anhydrous sodium sulphate and concentrated under reduced pressure to afford the title compound (1.5 g, 35%, HPLC purity 99.8%), mp: 141-143° C.

$^1$H-NMR ($CDCl_3$): δ 7.09-7.11 (m, 1H), 7.19 (s, 1H), 7.36-7.40 (m, 2H), 7.50-7.53 (m, 3H), 7.68-7.7 (d, 2H), 8.03-8.06 (d, 2H). MS m/z: 283.9 ($M^+$). IR (KBr) $cm^{-1}$: 1596 (—C═O).

Described below are the examples of pharmacological assays used for finding out the efficacy of the compounds of the present invention wherein their protocols and results are provided.

Rat Carrageenan Paw Edema Test

The carrageenan paw edema test was performed as described by Winter et al (Proc. Soc. Exp. Biol. Me., 111, 544, 1962). Male Wistar rats were selected and the body weight were equivalent within each group. The rats were fasted for eighteen hours with free access to water. The rats were dosed orally with the test compound suspended in vehicle containing 0.5% methylcellulose. The control rats were administered the vehicle alone. After one hour the rats were injected with 0.1 ml of 1% Carrageenan solution in 0.9% saline into the sub plantar surface of the right hind paw. Paw thickness was measured using vernier calipers at 0 time, after 2 and 3 hours. The average of foot swelling in drug treated animals was compared with that of control animals. Anti-inflammatory activity was expressed as the percentage inhibition of edema compared with control group [Arzneim-Forsch/Drug Res., 43(I), 1, 44-50,1993; Ottemess and Bliven, Laboratory Models for Testing NSAIDs, In Non-Steroidal Anti-Inflammatory Drugs, (J. Lombardino, ed.1985)]. The data of the selected compounds in this invention are summarized in Table I. In order to evaluate their role on the ulcer formation, the animals were sacrificed by cervical dislocation, the stomach removed and flushed with 1% formalin (10 ml). The stomach was opened along the greater curvature. The haemorrhagic puncta and sulci were identified macroscopically. The presence or absence of stomach lesions was scored. The incidence of ulceration was calculated from the number of rats that showed atleast one gastric ulcer or haemorrhagic erosion.

TABLE I

| Example No. | Rat Paw Edema model % Inhibition (10 mg/kg body weight) |
|---|---|
| 6 | 64 |
| 7 | 60.9 |
| 9 | 42.8 |
| 13 | 47.8 |
| 20 | 39.4 |

In Vitro Evaluation of Cycloxygenase-2 (COX-2) Inhibition Activity

The compounds of this invention exhibited in vitro inhibition of COX-2. The COX-2 inhibition activity of the compounds illustrated in the examples was determined by the following method.

Human Whole Blood Assay

Human whole blood provides a protein and cell rich milieu appropriate for the study of biochemical efficacy of anti-inflammatory compounds such as selective COX-2 inhibitors. Studies have shown that normal human blood does not contain COX-2 enzyme. This is correlating with the observation that COX-2 inhibitors have no effect on prostaglandin $E_2$ (PGE2) production in normal blood. These inhibitors are active only after incubation of human blood with lipopolysaccharide (LPS), which induces COX-2 production in the blood.

Method

Fresh blood was collected in tubes containing potassium EDTA by vein puncture from male volunteers. The subjects should have no apparent inflammatory conditions and not taken NSAIDs for atleast 7 days prior to blood collection. Blood was treated with aspirin in vitro (10 μg/ml, at time zero) to inactivate COX-1, and then with LPS (10 μg/ml) along with test agents or vehicle. The blood was incubated for 24 h at 37° C., after which the tubes were centrifuged, the plasma was separated and stored at −80° C. (J. Pharmacol. Exp. Ther., 271, 1705, 1994; Proc. Natl. Acad. Sci. USA., 96, 7563, 1999). The plasma was assayed for PGE2 using Cayman ELISA kit as per the procedure outlined by the manufacturer (Cayman Chemicals, Ann Arbor, USA). The plasma was also tested for TNF-α, IL-1β, and IL-6 using appropriate human ELISA kit as per the procedure of manufacturer (Cayman Chemicals, Ann Arbor, USA). Representative results of COX-2 inhibition are shown in Table II.

TABLE II

| Example No. | Conc. (μM) | COX-2 Inhibition (%) |
|---|---|---|
| 6 | 0.1 | 51.94 |
| 9 | 0.1 | 60.47 |
| 13 | 0.1 | 45.67 |

Tumor Necrosis Factor Alpha (TNF-α)

This assay determines the effect of test compounds on the production of TNF-α from human monocytes. Compounds were tested for their ability to downregulate the production of TNF-α in activated monocytes. Test compounds were incubated for three, six and twenty four hours with human monocytes. Lipopolysaccharide was used to stimulate the monocytes. The level of TNF-α was quantitated using Enzyme-Linked Immunosorbent assay performed in a 96 well format. Representative results of TNF-α inhibition are shown in Table III.

TABLE III

| Example No. | Conc. (μM) | TNF-α Inhibition (%) |
|---|---|---|
| 4 | 10 | 55.41 |
| 6 | 1 | 51.48 |
| 11 | 1 | 29.2 |
| 19 | 10 | 69.43 |
| 20 | 1 | 26.34 |

Interleukin-6(IL-6)

This assay determines the effect of test compounds on the production of IL-6 from human monocytes. Compounds are tested for their ability to downregulate the production of IL-6 in activated monocytes. Test compounds were incubated for three, six and twenty four hours with human monocytes. Lipopolysaccharide was used to stimulate the monocytes. The level of Interleukin-6 is quantitated using Enzyme-Linked Immunosorbent assay performed in a 96 well format. Representative results of IL-6 inhibition are shown in Table IV.

TABLE IV

| Example No. | Conc. (μM) | IL-6 Inhibition (%) |
|---|---|---|
| 1 | 1 | 62.52 |
| 2 | 1 | 62.34 |
| 21 | 1 | 67.47 |
| 22 | 1 | 52.28 |
| 24 | 10 | 66.01 |
| 32 | 10 | 53.33 |

Inhibitory Action on Adjuvant Arthritis

Compounds were assayed for their activity on rat adjuvant induced arthritis according to Theisen-Popp et al., (Agents Actions, 42, 50-55,1994). Six to seven weeks old, Wistar rats were weighed, marked and assigned to groups [a negative control group in which arthritis was not induced (non-adjuvant control), a vehicle-treated arthritis control group, test substance treated arthritis group]. Adjuvant induced arthritis was induced by an injection of *Mycobacterium butyricum* (Difco) suspended in liquid paraffin into the sub-plantar region of the right hind paw (J. Pharmacol. Exp. Ther., 284, 714, 1998). Body weight, contra-lateral paw volumes were determined at various days (0, 4, 14, 21) for all the groups. The test compound or vehicle was administered orally beginning post injection of adjuvant and continued for 21 days. On day 21, body weight and paw volume of both right and left hind paw, spleen, and thymus weights were determined. In addition, the radiograph of both hind paws was taken to assess the tibio-tarsal joint integrity. Hind limb below the stifle joint was removed and fixed in 1% formalin saline. At the end of the experiment, plasma samples were analysed for cytokines, interleukins and prostaglandins. The presence or absence of lesions in the stomachs was also observed.

Two-factor ('treatment' and 'time') Analysis of Variance with repeated measures on 'time' were applied to the % changes for body weight and foot volumes. A post hoc Dunnett's test was conducted to compare the effect of treatments to vehicle. A one-way Analysis of Variance was applied to the thymus and spleen weights followed by the Dunnett's test to compare the effect of treatments to vehicle. Dose-response curves for % inhibition in foot volumes on days 4, 14 and 21 were fitted by a 4-parameter logistic function using a nonlinear Least Squares' regression. $ID_{50}$ was defined as the dose corresponding to a 50% reduction from the vehicle and was derived by interpolation from the fitted 4-parameter equation.

DTP Human Tumor Cell Line Screen

Methodology Of The In Vitro Cancer Screen

The three cell line, one-dose prescreen carried out which identifies a large proportion of the compounds that would be inactive in multi-dose 60 cell line screening. The current assay utilizes a 384 well plate format and fluorescent staining technologies resulting in greater screening capacity for testing of synthetic samples.

Cell Lines

The cell lines of the cancer screening panel are grown in RPMI 1640 medium containing 5% fetal bovine serum and 2 mM L-glutamine. For a typical screening experiment, cells are inoculated into 96 well microtiter plates in 100 μL. After cell inoculation, the microtiter plates are incubated at 37° C., 5% $CO_2$, 95% air and 100% relative humidity for 24 h prior to addition of experimental drugs. The cells are plated a densities of 5000 cells/well (MCF7), 1000 cells/well (NCI-H460), and 7500 cells/well (SF-268) to allow for varying doubling time of the cell lines. Each plate contains all three cell lines, a series of dilutions of standard agents, total kill wells and appropriate controls. Plates are incubated under standard conditions for 24 hours prior to addition of experimental compounds or extracts.

Addition of Experimental Agents (Pure Compounds)

Experimental compounds are solubilized in dimethyl sulfoxide (DMSO) at 400-times the desired maximum test concentration (maximum final DMSO concentration of 0.25%) and stored frozen. Compounds are then diluted with complete media with 0.1% gentamicin sulfate (5 μl of test sample in 100% DMSO is added to 565 μl of complete medium). 20 μl of this solution is then dispensed into test wells containing 50 μl of cell suspension to yield a test concentration of 1.00E-04M.

Two standard drugs, meaning that their activities against the cell lines are well documented, are tested against each cell line: NSC 19893 (5-FU) and NSC 123127 (Adriamycin).

Endpoint Measurement

After compound addition, plates are incubated at standard conditions for ?hours, 10 μl/well Alamar Blue is added and the plates are incubated for an additional 4 hours. Fluorescence is measured using an excitation wavelength of 530 nm and an emission wavelength of 590 nm.

Calculation of Percent Test Cell Growth/Control (Untreated) Cell Growth (T/C)

Calculation of Percent Test Cell Growth/Control (Untreated) Cell Growth (T/C)

Percent growth is calculated on a plate-by-plate basis for test wells relative to control wells. Percent Growth is expressed as the ratio of fluorescence of the test well to the average fluorescence of the control wells ×100. The results are shown in table V.

TABLE V

| | Concentration (100 μm) Percentage Growth | | |
|---|---|---|---|
| Example No. | Lung NCI-H460 | Breast MCF7 | CNS SF-268 |
| 4 | 0 | 0 | 3 |
| 6 | 0 | 0 | 12 |
| 8 | 1 | 5 | 6 |
| 9 | 0 | 1 | 1 |
| 10 | 0 | 0 | 0 |
| 11 | 0 | 5 | 2 |
| 12 | 0 | −1 | 4 |

The invention claimed is:

1. A pyrimidine compound of the formula (I)

(I)

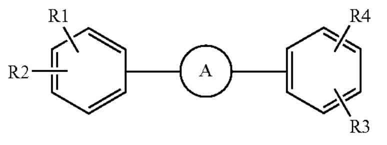

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine of the structure (i)

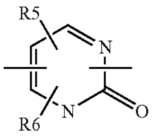

(ii)

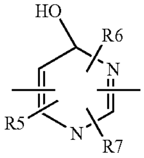

(iii)

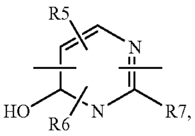

or (iv)

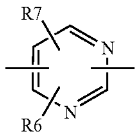

wherein $R_5$, $R_6$, $R_7$, may be same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl through carbon or nitrogen atom, wherein in structure (i) when at least one N is substituted, the substitution is not an alkyl, wherein in structure (iv) $R_6$ and $R_7$ are not hydrogen or an alkyl group, and wherein when one of $R_6$ and $R_7$ is a haloakyl group, the other is not a haloalkyl group and when one of $R_6$ and $R_7$ is an amino group the other is not an alkoxy, amino or amino substituted alkyl group.

2. A pyrimidine compound selected from the group consisting of:

4-Chloro-5,6-diphenyl-2-(trifluoromethyl)pyrimidine;
4-Chloro-6-(4-methylphenyl)-5-phenyl-2-(trifluoromethyl)pyrimidine;
4-Chloro-6-(4-fluorophenyl)-5-phenyl-2-(trifluoromethyl)pyrimidine;
4-Chloro-6-[4-(methylsulfonyl)phenyl]-5-phenyl-2-(trifluoromethyl)pyrimidine;
4-Chloro-5-(4-chlorophenyl)-6-[4-(methylsulfonyl)phenyl]-2-(trifluoromethyl)pyrimidine;
4-Chloro-5-(4-fluorophenyl)-6-[4-(methylsulfonyl)phenyl]-2-(trifluoromethyl)pyrimidine;

2,4-Dichloro-5,6-diphenylpyrimidine;
2,4-Dichloro-6-(4-methylphenyl)-5-phenylpyrimidine;
6-(4-Chlorophenyl)-2,4-dichloro-5-phenylpyrimidine;
5-(4-Chlorophenyl)-2,4-dichloro-6-phenylpyrimidine;
2,4-Dichloro-5-(4-methoxyphenyl)-6-phenylpyrimidine;
2,4-Dichloro-5-[4-(methylthio)phenyl]-6-phenylpyrimidine;
2,4-Dichloro-6-(4-chlorophenyl)-5-[4-(methylthio)phenyl]pyrimidine;
2,4-Dichloro-5-(4-chlorophenyl)-6-(4-methylphenyl)pyrimidine;
4-Azido-5,6-diphenyl-2-(trifluoromethyl)pyrimidine;
4-Azido-6-[4-(methylsulfonyl)phenyl]-5-phenyl-2-(trifluoromethyl)pyrimidine;
4-Azido-5-(4-chlorophenyl)-6-[4-(methylsulfonyl)phenyl]-2-(trifluoromethyl)pyrimidine;
4-Azido-5-(4-fluorophenyl)-6-[4-(methylsulfonyl)phenyl]-2-(trifluoromethyl)pyrimidine;
2,4-Diazido-5,6-diphenylpyrimidine;
2,4-Diazido-5-(4-chlorophenyl)-6-phenylpyrimidine;
4-Hydrazino-5,6-diphenyl-2-(trifluoromethyl)pyrimidine;
4-Hydrazino-6-(4-methylphenyl)-5-phenyl-2-(trifluoromethyl)pyrimidine;
4-Hydrazino-6-(4-fluorophenyl)-5-phenyl-2-(trifluoromethyl)pyrimidine;
4-Hydrazino-6-[4-(methylsulfonyl)phenyl]-5-phenyl-2-(trifluoromethyl)pyrimidine;
5-(4-Chlorophenyl)-4-hydrazino-6-[4-(methylsulfonyl)phenyl]-2-(trifluoromethyl)pyrimidine;
5-(4-Fluorophenyl)-4-hydrazino-6-[4-(methylsulfonyl)phenyl]-2-(trifluoromethyl)pyrimidine;
2-Chloro-5,6-diphenyl-4-hydrazinopyrimidine;
2-Chloro-4-hydrazino-5-[4-(methylthio)phenyl]-6-phenylpyrimidine;
2,4-Dihydrazino-5,6-diphenylpyrimidine;
2,4-Dihydrazino-5-[4-(methylthio)phenyl]-6-phenylpyrimidine;
N'-[5,6-Diphenyl-2-(trifluoromethyl)pyrimidin-4-yl]acetohydrazide;
N'-[6-(4-Methylphenyl)-5-phenyl-2-(trifluoromethyl)pyrimidin-4-yl]acetohydrazide;
N'-[6-(4-Fluorophenyl)-5-phenyl-2-(trifluoromethyl)pyrimidin-4-yl]acetohydrazide;
N"-[6-[4-(Methylsulfonyl)phenyl]-5-phenyl-2-(trifluoromethyl)pyrimidin-4-yl]acetohydrazide;
N'-[5-(4-Chlorophenyl)-6-[4-(methylsulfonyl)phenyl]-2-(trifluoromethyl)pyrimidin-4-yl]acetohydrazide;
N'-[5-(6-Fluorophenyl)-6-[4-(methylsulfonyl)phenyl]-2-(trifluoromethyl)pyrimidin-4-yl]acetohydrazide;
N'-[5-(4-Chlorophenyl)-[6-(4-methylsulfonyl)phenyl]-2-(trifluoromethyl)pyrimidin-4-yl]trifluoroacetohydrazide;
4-Chloro- 1,6-diphenylpyrimidine-2(1H)-one;
4-Azido-6-[(4-methylthio)phenyl]-1-phenylpyrimidin-2(1H)-one;
4-[3-(4-Chlorophenyl)-2-oxo-6-trifluoromethyl-2,3-dihydro-pyrimidin-4-yl]benzenesulfonamide;
6-(4-Methylsulfonylphenyl)-1-p-tolyl-4-(trifluoromethy) pyrimidin-2(1H)-one;
4-Azido-6-(4-methylsulfonylphenyl)-1-p-tolyl-pyrimidin-2(1H)-one;
4-(6-Azido-3-methoxyphenyl-2-oxo-2,3-dihydropyrimidin-4-yl)benzenesulfonamide;
4-(6-Azido-4-methoxyphenyl-2-oxo-2,3-dihydropyrimidin-4-yl)benzenesulfonamide;

2-Chloro-5-(4-chlorophenyl)-4-methylthio-6-[(4-methylthio)phenyl]pyrimidine;
6-[(4-Methylthio)phenyl]-1-phenyl-4-(trifluoromethyl)pyrimidin-2(1H)-one;
4-(2-Oxo-3-phenyl-6-trifluoromethyl-2,3-dihydropyrimidin-4-yl)benzenesulfonamide;
4-Methylthio-5,6-bis(p-tolyl)pyrimidine;
4-Methylthio-5,6-diphenyl-pyrimidin-2-ol;
4-Methylsulfonyl-5,6-bis(p-tolyl)pyrimidine;
1,6-Diphenyl-4-(trifluoromethyl)pyrimidin-2(1H)-one;
4-(2-Hydroxy-6-methylthio-5-phenylpyrimidin-4-yl)benzenesulfonamide;
4-Methylthio-6-[(4-methylthio)phenyl]-5-phenylpyrimidine;
2-Chloro-4-methylthio-5,6-bis(p-tolyl)pyrimidine;
2-Chloro-4-methylthio-6-[(4-methylthio)phenyl]-5-p-tolyl-pyrimidine;
5-(4-Bromophenyl)-2-chloro-4-methylthio-6-[(4-methylthio)phenyl]pyrimidine;
5-(2-Bromophenyl)-4-methylthio-6-[(4-methylthio)phenyl]pyrimidin-2-ol;
4-(2-Chloro-6-methylthio-5-phenylpyrimidin-4-yl)benzenesulfonamide;
2-Chloro-4,5-bis-(4-methoxyphenyl)-6-(methylthio)pyrimidine;
2-Chloro-4-methylthio-6-[(4-methylthio)phenyl]-5-phenylpyrimidine;
2,4-Diazido-6[(4-methylthio)phenyl)]-5-phenylpyrimidine;
2,4-Diazido-5-(4-bromophenyl)-6-(4-methylthiophenyl)pyrimidine;
4-Chloro-6-[(4-methylsulfonyl)phenyl]-1-phenylpyrimidin-2(1H)-one;
4-Azido-1-(2-fluorophenyl)-6-[(4-methylthio)phenyl]-pyrimidin-2(1H)-one;
2-[(4-Methylsulfonyl)phenyl]-6-trifluoromethyl-3-[(4-trifluoromethyl)phenyl]-3,4-dihydropyrimidin-4-ol;
5-(3-Fluorophenyl)-4-methylthio-6-[(4-methylthio)phenyl]pyrimidin-2-ol, and
4-(6-Hydroxy-6-methyl-2-p-tolyl-4-trifluoromethyl-6H-pyrimidin-1-yl)benzenesulfonamide.

3. A process for the preparation of a pyrimidine compound of the formula (I)

(I)

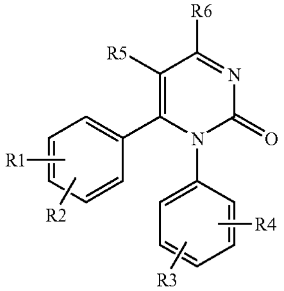

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; $R_5$, $R_6$, may be same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the process comprising condensing a compound of formula (Ia) using a solvent in an acidic condition in the presence of a phase transfer catalyst and under cooling to reflux conditions, (Ia)

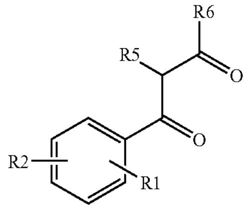

wherein all symbols are as defined above with a compound of the formula (Ib)

(Ib)

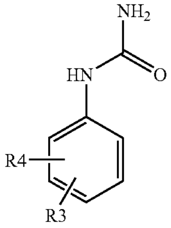

where all symbols are as defined above.

4. A process for the preparation of a pyrimidine compound of the formula (I)

(I)

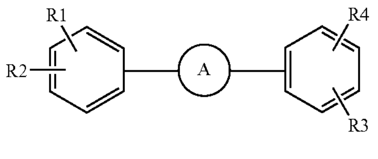

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine of the structure (i)

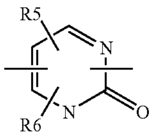

or (iv)

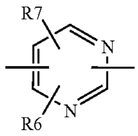

wherein $R^6$ represents halogen atom, $R_5$, $R_7$, may be same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl through carbon or nitrogen atom, wherein in structure (i) when at least one N is substituted, the substitution is not an alkyl, and wherein in structure (iv) $R_6$ and $R_7$ are not hydrogen and when one of $R_6$ and $R_7$ is a haloalkyl, the other is not a haloalkyl, the other is not a haloalkyl; the process comprising converting the compound of formula (Ic) using a reagent, in the presence or absence of a solvent, and in the presence or absence of DMF, N,N-dimethyl aniline or N,N-diethyl aniline at a temperature of from 20° C. to reflux temperature, in a range of from 2 hours to 5 hours, (Ic)

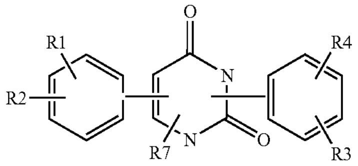

wherein all symbols are as defined earlier.

5. A process for the preparation of a pyrimidine compound of the formula (I)

(I)

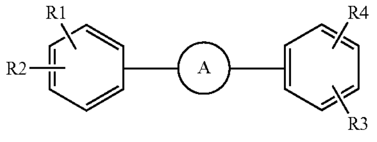

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine of the formula

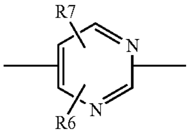

wherein any of $R^7$ represents halogen atom and $R^6$ represents hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl through carbon or nitrogen atom, wherein in structure (iv) $R_6$ and $R_7$ are not hydrogen and when one of $R_6$ and $R_7$ is a haloalkyl, the other is not a haloalkyl; the process comprising converting the compound of formula (Id) using a reagent in the presence or absence of a solvent, and in the presence or absence of DMF, N,N-dimethyl aniline or N,N-diethyl aniline at a temperature of from 20° C. to reflux temperature, in a range of from 2 hours to 12 hours, (Id)

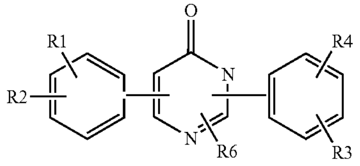

wherein $R^6$ is as defined above.

6. A process for the preparation of a pyrimidine compound of the formula (I)

(I)

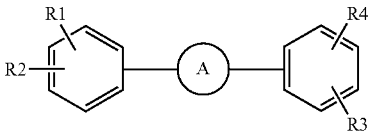

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine of the structure (i)

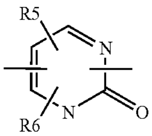

or

-continued (iv)

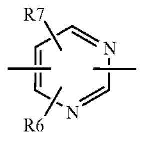

wherein $R^6$ represents azido, hydrazine or hydrazine derivatives, $R^5$ and $R^7$ are same or different and represent hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl through carbon or nitrogen atom, wherein in structure (i) when at least one N is substituted, the substitution is not an alkyl, and wherein in structure (iv) $R_6$ and $R_7$ are not hydrogen and when one of $R_6$ and $R_7$ is a haloalkyl, the other is not a haloalkyl; the process comprising converting the compound of formula (Ie) in a presence of one or more equivalents of a metal azide or a hydrazine and a solvent, at a temperature of from 80° C. to 100° C. from 0.5 hour to 18 hours, (Ie)

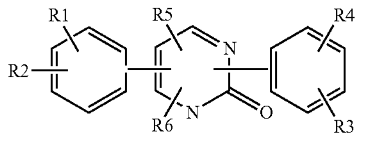

or (Ie)

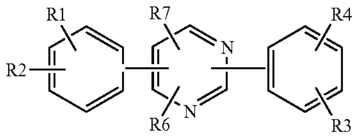

wherein $R^6$ represents halogen atom and all other symbols are as defined above.

7. A process for the preparation of a pyrimidine compound of the formula (I)

(I)

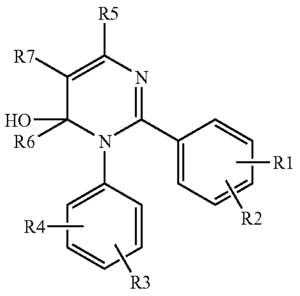

or

-continued (I)

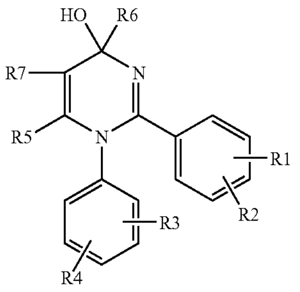

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives;

wherein $R_5$, $R_6$, $R_7$, may be same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the process comprising reacting a compound of the formula (If)

(If)

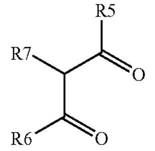

where all symbols are as defined above, with a compound of formula (Ig) using an agent selected from the group consisting of polyphosphoric acid, phosphorous pentoxide and sulfuric acid in a solvent, under acid or base catalyzed conditions in the presence of a phase transfer catalyst, and under cooling to reflux conditions, (Ig)

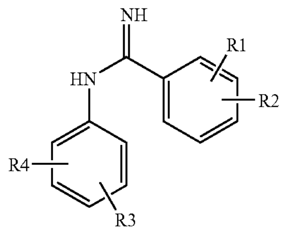

where all symbols are as defined above.

8. A process for the preparation of a pyrimidine compound of the formula (I)

(I)

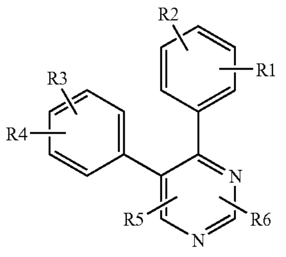

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives;

wherein $R_5$, $R_6$, are same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives, wherein in structure (iv) $R_6$ and $R_7$ are not hydrogen and when one of $R_6$ and $R_7$ is a haloalkyl, the other is not a haloalkyl; the process comprising:

i) reacting a compound of formula (Ih)

(Ih)

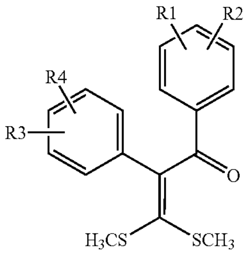

where all symbols are as defined earlier with a compound of formula (Ii) in a solvent under acid or base catalyzed conditions, in the presence of a phase transfer catalyst, and under cooling to reflux conditions, (Ii)

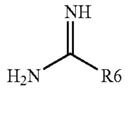

where $R^6$ is as defined earlier to produce compound of formula (Ij)

(Ij)

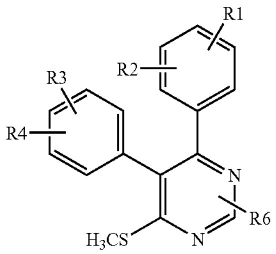

and ii) converting the compound of formula (Ij) to produce compound of formula (I), where all symbols are as defined earlier, by reacting with suitable nucleophilic reagent.

9. A process for the preparation of a pyrimidine compound of the formula (I)

(I)

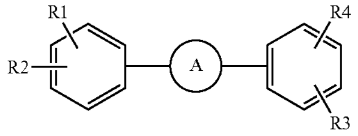

and their pharmaceutically acceptable salts, wherein $R_1$, $R_2$, $R_3$ and $R_4$ may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine of the structure (i)

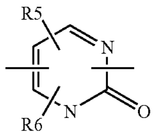

(ii)

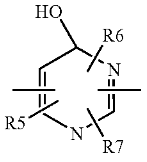

(iii)

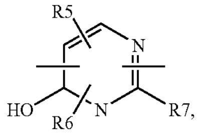

or

-continued (iv)

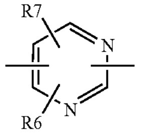

wherein any one of $R_5$, $R_6$, $R_7$, represent hydrazine derivatives and the other $R_5$, $R_6$, $R_7$, are same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl through carbon or nitrogen atom, wherein in structure (i) when at least one N is substituted, the substitution is not an alkyl, and wherein in structure (iv) $R_6$ and $R_7$ are not hydrogen and when one of $R_6$ and $R_7$ is a haloalkyl, the other is not a haloalkyl; the process comprising reacting the compound of formula (I) wherein any one of $R_5$, $R_6$, $R_7$ represent hydrazine, using a reagent in a solvent an at from room temperature to reflux temperatures of the solvent.

10. A process for the preparation of a pyrimidine compound of the formula (I)

(I)

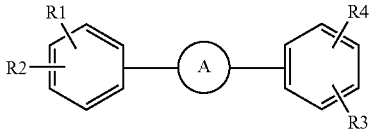

and their pharmaceutically acceptable salts, wherein any one of $R_1$, $R_2$, $R_3$ and $R_4$ represent alkylsulfonyl, alkylsulfinyl, aryl sulfinyl or arylsulfonyl and the other $R_1$, $R_2$, $R_3$ and $R_4$ are same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine derivative of the structure (i)

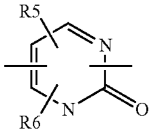

-continued (ii)

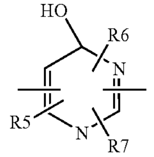

(iii)

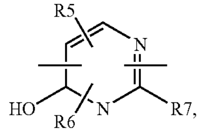

, or (iv)

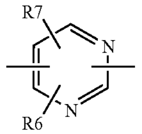

wherein any one of $R_5$, $R_6$, $R_7$, represent alkylsulfonyl, alkylsulfinyl, aryl sulfinyl or arylsulfonyl and the other $R_5$, $R_6$, $R_7$, are same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl through carbon or nitrogen atom, wherein in structure (i) when at least one N is substituted, the substitution is not an alkyl, and wherein in structure (iv) $R_6$ and $R_7$ are not hydrogen and when one of $R_6$ and $R_7$ is a haloalkyl, the other is not a haloalkyl; the process comprising reacting the compound of formula (I) wherein the groups any of the groups $R_1$, $R_2$, $R_3$, $R_4$, $R_5$, $R_6$ represent alkylthio or arylthio and all other symbols are as defined above, using a reagent in a solvent that does not adversely invluence the reaction, and under cooling to refluxing conditions.

11. A process for the preparation of a pyrimidine compound of the formula (I)

(I)

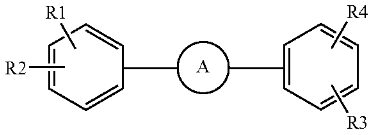

and their pharmaceutically acceptable salts, wherein any one of $R_1$, $R_2$, $R_3$ and $R_4$ represent sulfamoyl and the other $R_1$, $R_2$, $R_3$ and $R_4$ are same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsufonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine of the structure (i)

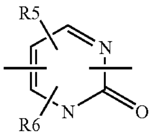

(ii)

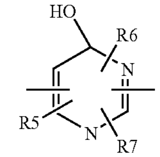

(iii)

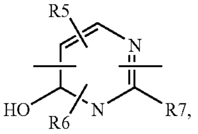

or (iv)

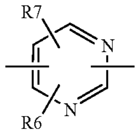

wherein any one of $R_5$, $R_6$, $R_7$, represent sulfamoyl and the other $R_5$, $R_6$, $R_7$, are same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl through carbon or nitrogen atom, wherein in structure (i) when at least one N is substituted, the substitution is not an alkyl, and wherein in structure (iv) $R_6$ and $R_7$ are not hydrogen and when one of $R_6$ and $R_7$ is a haloalkyl, the other is not a haloalkyl; the process comprising reacting the compound of formula (D wherein the groups any of the groups $R_1$, $R_2$, $R_3$, $R_4$, $R_5$, $R_6$ represent alkylsulfonyl and all other symbols are as defined above, using a reagent in the presence of sodium acetate and water, at a temperature of from 0° C. to room temperature for a time of from 2 hours to 4 hours, wherein the reagent is hydroxylamine-O-sulfonic acid.

12. A pharmaceutical composition, which comprises a compound of formula (I)

(I)

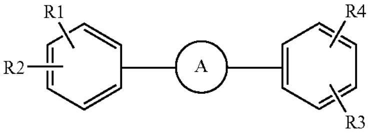

as defined in claim 1 and a pharmaceutically acceptable carrier, diluent, excipient or solvate.

13. A pharmaceutical composition as claimed in claim 12, in the form of a tablet, capsule, powder, syrup, solution, aerosol or suspension.

14. A pharmaceutical composition which comprises a compound as claimed in claim 2 and a pharmaceutically acceptable carrier, diluent, excipient or solvate.

15. A method for treatment of pain, rheumatoid arthritis, breast cancer, lung cancer or CNS cancer, the method comprising administering the compound of formula (I) as claimed in claim 1, together with a pharmaceutically acceptable carrier, diluent, excipient or solvate to a patient in need thereof.

16. A method for treatment of pain, rheumatoid arthritis, breast cancer, lung cancer or CNS cancer, the method comprising administering the compound as claimed in claim 2, together with a pharmaceutically acceptable carrier, diluent, excipient or solvate to a patient in need thereof.

17. A method for treatment of pain, rheumatoid arthritis, breast cancer, lung cancer, or CNS cancer, the method comprising administering the composition as claimed in claim 12 to a patient in need thereof.

18. A method for treatment of a pain disorder, comprising administering the compound of formula (I) as claimed in claim 1.

19. A method for treatment of a pain disorder, comprising administering the compound as claimed in claim 2.

20. A method for treatment of a pain disorder, comprising administering the composition as claimed in claim 12.

* * * * *